(12) United States Patent
Sridhar et al.

(10) Patent No.: US 11,083,401 B2
(45) Date of Patent: Aug. 10, 2021

(54) ELECTRIC FIELD ENCEPHALOGRAPHY: ELECTRIC FIELD BASED BRAIN SIGNAL DETECTION AND MONITORING

(75) Inventors: Srinivas Sridhar, Newton, MA (US); Yury Petrov, Wakefield, MA (US); Ozgur Yavuzcetin, Malden, MA (US)

(73) Assignee: Northeastern University, Boston, MA (US)

( * ) Notice: Subject to any disclaimer, the term of this patent is extended or adjusted under 35 U.S.C. 154(b) by 1363 days.

(21) Appl. No.: 14/420,613

(22) PCT Filed: Aug. 9, 2012

(86) PCT No.: PCT/US2012/050184
§ 371 (c)(1),
(2), (4) Date: Dec. 2, 2015

(87) PCT Pub. No.: WO2014/025353
PCT Pub. Date: Feb. 13, 2014

(65) Prior Publication Data
US 2016/0081577 A1    Mar. 24, 2016

(51) Int. Cl.
*A61B 5/00*    (2006.01)
*A61B 5/24*    (2021.01)
(Continued)

(52) U.S. Cl.
CPC ............. *A61B 5/291* (2021.01); *A61B 5/24* (2021.01); *A61B 5/316* (2021.01); *A61B 5/4064* (2013.01); *A61B 5/4088* (2013.01); *A61B 5/4094* (2013.01); *A61B 5/6803* (2013.01); *A61B 5/7203* (2013.01); *A61B 5/742* (2013.01);
(Continued)

(58) Field of Classification Search
None
See application file for complete search history.

(56) References Cited

U.S. PATENT DOCUMENTS 3,565,060 A   2/1971   Sipple
4,559,950 A   12/1985  Vaughan et al.
(Continued)

FOREIGN PATENT DOCUMENTS

EP   1615550 B1    3/2007
JP   2011-136158 A 7/2011
(Continued)

OTHER PUBLICATIONS

Baillet, S. et al., "Combined MEG and EEG source imaging by minimization of mutual information," IEEE Trans. Biomed. Eng., vol. 46, No. 5, pp. 522-534 (May 1999).
(Continued)

*Primary Examiner* — Etsub D Berhanu
(74) *Attorney, Agent, or Firm* — Verrill Dana, LLP

(57) ABSTRACT

Systems and methods for measuring brain activity of a subject are disclosed, comprising: positioning a plurality of electric field sensors at multiple positions on the exterior of a skull of the subject; measuring one to three components of a plurality of instantaneous electric field vectors generated by a plurality of electric field sources, the electric field vectors being measured by the plurality of electric field sensors; and determining brain activity of the subject based on the measurement of the plurality of instantaneous electric field vectors.

28 Claims, 25 Drawing Sheets

(51) Int. Cl.
*A61B 5/291* (2021.01)
*A61B 5/316* (2021.01)

(52) U.S. Cl.
CPC ..... *A61B 5/6814* (2013.01); *A61B 2562/0215* (2017.08); *A61B 2562/046* (2013.01)

(56) References Cited

U.S. PATENT DOCUMENTS

| | | | |
|---|---|---|---|
| 4,649,482 | A | 3/1987 | Raviv et al. |
| 4,791,593 | A | 12/1988 | Hennion |
| 4,800,888 | A | 1/1989 | Itil et al. |
| 5,148,149 | A | 9/1992 | Campbell et al. |
| 5,613,495 | A | 3/1997 | Mills et al. |
| 5,704,365 | A | 1/1998 | Albrecht et al. |
| 5,724,984 | A | 3/1998 | Arnold et al. |
| 5,797,853 | A | 8/1998 | Musha et al. |
| 6,161,030 | A | 12/2000 | Levendowski et al. |
| 6,195,576 | B1 | 2/2001 | John |
| 6,449,461 | B1 | 9/2002 | Otten |
| 6,807,438 | B1 | 10/2004 | Brun Del Re et al. |
| 6,871,084 | B1 | 3/2005 | Kingsley et al. |
| 6,873,872 | B2 | 3/2005 | Gluckman et al. |
| 7,141,987 | B2 | 11/2006 | Hibbs et al. |
| 8,032,209 | B2 | 10/2011 | He et al. |
| 8,190,248 | B2 | 5/2012 | Besio et al. |
| 8,437,843 | B1 | 5/2013 | Kayyali et al. |
| 2003/0021518 | A1* | 1/2003 | Smirnov ............... B82Y 10/00 385/15 |
| 2003/0093129 | A1 | 5/2003 | Nicolelis et al. |
| 2003/0204148 | A1 | 10/2003 | Lange et al. |
| 2004/0097802 | A1 | 5/2004 | Cohen |
| 2004/0158119 | A1 | 8/2004 | Osorio et al. |
| 2005/0073322 | A1 | 4/2005 | Hibbs et al. |
| 2005/0215916 | A1 | 9/2005 | Fadem et al. |
| 2006/0173510 | A1* | 8/2006 | Besio ................... A61B 5/0482 607/45 |
| 2006/0251303 | A1* | 11/2006 | He ...................... A61B 5/04008 382/128 |
| 2007/0048707 | A1 | 3/2007 | Caamano et al. |
| 2007/0073184 | A1 | 3/2007 | Lu et al. |
| 2007/0106143 | A1 | 5/2007 | Flaherty |
| 2007/0225585 | A1* | 9/2007 | Washbon ............. A61B 5/0478 600/393 |
| 2007/0250134 | A1 | 10/2007 | Miesel et al. |
| 2009/0177073 | A1 | 7/2009 | Sonnenborg |
| 2009/0182220 | A1* | 7/2009 | Blunt .................... G06T 11/006 600/409 |
| 2010/0100153 | A1 | 4/2010 | Carlson et al. |
| 2010/0113961 | A1 | 5/2010 | Ohlander et al. |
| 2010/0145176 | A1 | 6/2010 | Himes |
| 2011/0190625 | A1 | 8/2011 | Harlev et al. |
| 2011/0282231 | A1 | 11/2011 | Pradeep et al. |
| 2011/0295096 | A1 | 12/2011 | Bibian et al. |
| 2012/0116725 | A1 | 5/2012 | Klinkenbusch |
| 2012/0136273 | A1* | 5/2012 | Michelson, Jr. ..... A61B 5/0478 600/544 |
| 2012/0302858 | A1 | 11/2012 | Kidmose et al. |
| 2012/0316459 | A1 | 12/2012 | Abreu |
| 2013/0009783 | A1 | 1/2013 | Tran |
| 2013/0035578 | A1 | 2/2013 | Chiu et al. |
| 2013/0079860 | A1 | 3/2013 | Besio |
| 2013/0138010 | A1 | 5/2013 | Nierenberg et al. |
| 2013/0310676 | A1 | 11/2013 | Jung |

FOREIGN PATENT DOCUMENTS

| | | | | |
|---|---|---|---|---|
| WO | WO-2011056626 | A1 * | 5/2011 | ........... A61B 5/0478 |
| WO | WO-2011088227 | A1 * | 7/2011 | ......... A61B 5/04008 |
| WO | WO-2012/068493 | A1 | 5/2012 | |

OTHER PUBLICATIONS

Gibson, R.S., "Slab-Coupled Optical Fiber Sensors for Electric Field Sensing Applications," All Theses and Dissertations, Paper 1942, 164 pages (Dec. 2009).

Gutierrez-Martinez, C. et al., "Modeling and experimental electro-optic response of dielectric lithium niobate waveguides used as electric field sensors," Measurement Science and Technology, vol. 22, 035207 (7 pgs.) (Feb. 15, 2011).

Haueisen, J. et al., "The Influence of Brain Tissue Anisotropy on Human EEG and MEG," NeuroImage, vol. 15, pp. 159-166 (2002).

Komssi, S. et al., "EEG minimum-norm estimation compared with MEG dipole fitting in the localization of somatosensory sources at S1," Clinical Neurophysiology, vol. 115, pp. 534-542 (2004).

Liu, A. K. et al., "Monte Carlo simulation studies of EEG and MEG localization accuracy," Human Brain Mapping, vol. 16, pp. 47-62 (2002).

Malmivuo, J., "Comparison of the properties of EEG and MEG in detecting the electric activity of the brain," Brain Topogr., vol. 25, pp. 1-19 (Jan. 2012).

Prance, R. J. et al., "Remote detection of human electrophysiological signals using electric potential sensors," Applied Physics Letters, vol. 93, pp. 033906-1-033906-3 (2008).

Ramon, C. et al., "Influence of head models on neuromagnetic fields and inverse source localizations," BioMedical Engineering Online, vol. 5, No. 55, pp. 1-13 (2006).

Runde, D. et al., "Integrated optical electric field sensor based on a Bragg grating in lithium niobate," Applied Physics B., Laser and Optics, vol. 86, pp. 91-95 (2007).

Wolters, C. H. et al., "Influence of tissue conductivity anisotropy on EEG/MEG field and return current computation in a realistic head model: A simulation and visualization study using high-resolution finite element modeling," NeuroImage, vol. 30, pp. 813-826 (2006).

Extended European Search Report issued by the European Patent Office for European Patent Application No. 12882612.0 dated Mar. 3, 2016 (8 pgs.).

L. H. Kahane, et al., "Regression Basics Chapter 2: The Least-Squares Estimation Method", Second Edition, Sage Publications, Inc. 2008, Retrieved from the internet: <URL: http://www.sagepub.com/upm-data/17668_Chapter2.pdf>, 22 pgs.

Y. Petrov, "Harmony: EEG/MEG Linear Inverse Source Reconstruction in the Anatomical Basis of Spherical Harmonics", PLOS ONE, Oct. 2012, vol. 7, Issue 10, 15 pgs.

R. Doost-Mohammady, et al., "Enhancing Wireless Medical Telemetry through Dynamic Spectrum Access", Proc. of IEEE ICC, Jun. 2012, pp. 1603-1608.

R. Doost-Mohammady, et al., "Transforming Healthcare and Medical Telemetry through Cognitive Radio Networks", IEEE Wireless Communications Magazine, Aug. 2012, vol. 19, No. 4, pp. 67-73.

C. E. Vasios, et al., "EEG/(f)MRI measurements at 7 Tesla using a New EEG cap (InkCAp)", NeuroImage, Dec. 2006, vol. 33, Issue 4, pp. 1082-1092.

O. Vaisanen, et al., "Improving the SNR of EEG generated by deep sources with weighted multi-electrode leads", Journal of Physiology-Paris, Nov. 2009, vol. 103, Issue 6, pp. 306-314.

P. L. Nunez, et al., "EEG coherency II: experimental comparisons of multiple measures", Clinical Neurophysiology, (1999) , vol. 110, pp. 469-486.

A. B. Usakli, "Improvement of EEG Signal Acquisition: An Electrical Aspect for State of the Art of Front End", Computational Intelligence and Neuroscience, Jan. 2010, vol. 2010, 7 pgs.

Y. Petrov, et al., "Ultra-dense EEG sampling results in two-fold increase of functional brain information", Neuroimage, (2014), vol. 90, pp. 140-145.

Kamrunnahar, M. et al., "Toward a Model-Based Predictive Controller Design in Brain-Computer Interfaces", Annals of Biomedical Engineering, May 2011, vol. 39, No. 5, pp. 1482-1492.

* cited by examiner

ELECTRIC FIELD ENCEPHALOGRAPHY: ELECTRIC FIELD BASED BRAIN SIGNAL DETECTION AND MONITORING

CROSS REFERENCE TO RELATED APPLICATIONS

This application is a National Stage Entry of PCT International Application No. PCT/US2012/050184, filed Aug. 9, 2012, the contents of which is incorporated herein by reference in its entirety.

FIELD OF THE DISCLOSURE

This application relates to the field of detection and monitoring of brain signals, and more particularly to detection and monitoring of electric fields generated by the brain. In this disclosure, methods and apparatuses to measure and analyze the components of the electric field vectors around the scalp are described.

BACKGROUND

Electro-encephalography (EEG) and magneto-encephalography (MEG) are well-established modalities of studying brain signals. EEG samples electric potential across the scalp, while MEG samples magnetic field (usually, one of its component) several centimeters away from the head surface. High-density implementations of these methods typically use 64-256 sensors covering the top half of the head. Several recent studies compared the two experimental techniques in terms of their spatial resolution and the amount of information they offer about the underlying brain activity. EEG and MEG were found to be similar in these respects (Liu et al., 2002; Haueisen et al., 2002; Komssi et al., 2004; Malmivuo, 2011) despite the fact that MEG is likely to be less affected by the skull's low conductivity than EEG (Wolters et al. 2006, but also see Ramon et al. 2006).

EEG and MEG provide somewhat different information on the brain's activity: MEG is sensitive to only tangential sources (with respect to MEG sensors), while EEG is sensitive to both radial and (less so) tangential sources (with respect to the scalp surface) (Ahlfors et al., 2010). Therefore, it is not surprising that recording both EEG and MEG signals can provide additional information on the brain's activity by increasing the effective number of independent signals recorded (Baillet et al., 1999; Malmivuo, 2011). It is well known that the high resistivity of the human skull produces a strong low-pass spatial filtering effect on EEG signals, which results in a lot of crosstalk among EEG electrodes.

Unlike EEG, which measures a single number, the electric potential at each spatial point, it would be advantageous to measure all 3 components of the electric field at each spatial point. Electric fields associated with brain activity have not previously been studied in detail because of the difficulty of measuring these weak signals. Furthermore, the electric field vector is given by the negative gradient of electric potential measured by EEG, and measuring electric field instead of its potential provides new information. Therefore, there remains a need for methods and systems that measure all three components of the electric field.

SUMMARY OF THE DISCLOSURE

Systems and methods for measuring brain activity of a subject are disclosed. The distribution of electric fields near the scalp is modeled, and the use of these fields for functional brain imaging or for measuring brain activity is described herein. The methods and apparatuses disclosed herein are referred to as Electric Field Encephalography ("EFEG"). In one embodiment, a method is disclosed comprising: positioning a plurality of electric field sensors at multiple positions on the exterior of a skull of the subject; measuring one to three components of a plurality of instantaneous electric field vectors generated by a plurality of electric field sources, the electric field vectors being measured by the plurality of electric field sensors; and determining brain activity of the subject based on the measurement of the plurality of instantaneous electric field vectors.

Estimating a location of each electric field source may be performed from data generated from the plurality of electric field sensors, each electric field source corresponding to a distinguishable data channel. A real-time image of brain activity may be generated. The subject may suffer from a neurological condition, such as Alzheimer's disease, traumatic brain injury, autism, or epilepsy. A comparison of the brain activity of the subject to the brain activity of a normal subject may be performed, and this comparison may be used to detect a neurological condition.

In another embodiment, a sensor apparatus for monitoring brain activity of a subject is disclosed, comprising: a plurality of electric field sensors configured to measure a plurality of instantaneous electric field vectors, the plurality of electric field sensors are distributed evenly at a plurality of locations on the exterior of a skull of the subject, the instantaneous electric field vectors including at least one of tangential, azimuthal and radial components; a computer for processing the measured electric field vectors, the computer comprising at least one processor and a memory providing code to the at least one processor configured to: estimate the noisiness of each electric field sensor using data from at least one of the plurality of electric field sensors, and identify sources for the measured electric field vectors.

Estimation of a three-dimensional location for each electric field source from data generated from the plurality of electric field sensors, and generation of a real-time, multi-channel image of brain activity, may also be performed. The image may be a three-dimensional image. Noisiness and channel cross-talk estimation may be performed for each electric field sensor by cross-correlating information from each of the plurality of electric field sensors. The plurality of electric field sensors may include tri-polar or multi-polar electrode sensors made of silver chloride (AgCl) or other materials, or electro-optical sensors such as photonic crystals made of lithium niobate or any other type of electric field sensor.

Repeated measurement of the components of an electric field vector may be performed to monitor brain activity over time. Generation of a map of brain activity, or a real-time map of brain activity, may be performed using the three-dimensional location data. Estimation of a location of each electric field source may also include using a mathematical model of head electrical characteristics for estimating the three-dimensional location data.

The plurality of electric field sensors may include at least 128 sensors. A cap may be used for conforming to the shape of the skull in which the plurality of sensors are embedded. At least one conduit may be used for transmitting the measured electric field vectors measured by the electric field sensors to the computer. The processor may be configured to display the image. A display may be used for the subject to visualize a pattern. A time resolution of 1 millisecond may be provided. Measurement of a signal from the plurality of electric field sensors in real-time may be performed to determine noise levels. Positioning the plurality of electric field sensors on the skull of the subject may allow the measurement of the plurality of instantaneous electric field vectors.

A pattern may be displayed that may be viewed by the subject while simultaneously measuring a plurality of instantaneous electric field vectors. Estimation of a three-dimensional location of each electric field source may include processing the plurality of electrical field vectors. A plurality of electric field sensors may include tri-polar electrode sensors or electro-optical sensors. The electro-optical sensors may be photonic crystals or Mach-Zehnder interferometers made in an electro-optic material. The Mach-Zehnder interferometers may be lithium niobate (LiNbO3). The tri-polar electrode sensors may be made of silver chloride (AgCl), may be 1-15 mm long and separated by 1-15 mm distances, and may be attached to a plastic disk.

DETAILED DESCRIPTION

1. General

Figure 1:
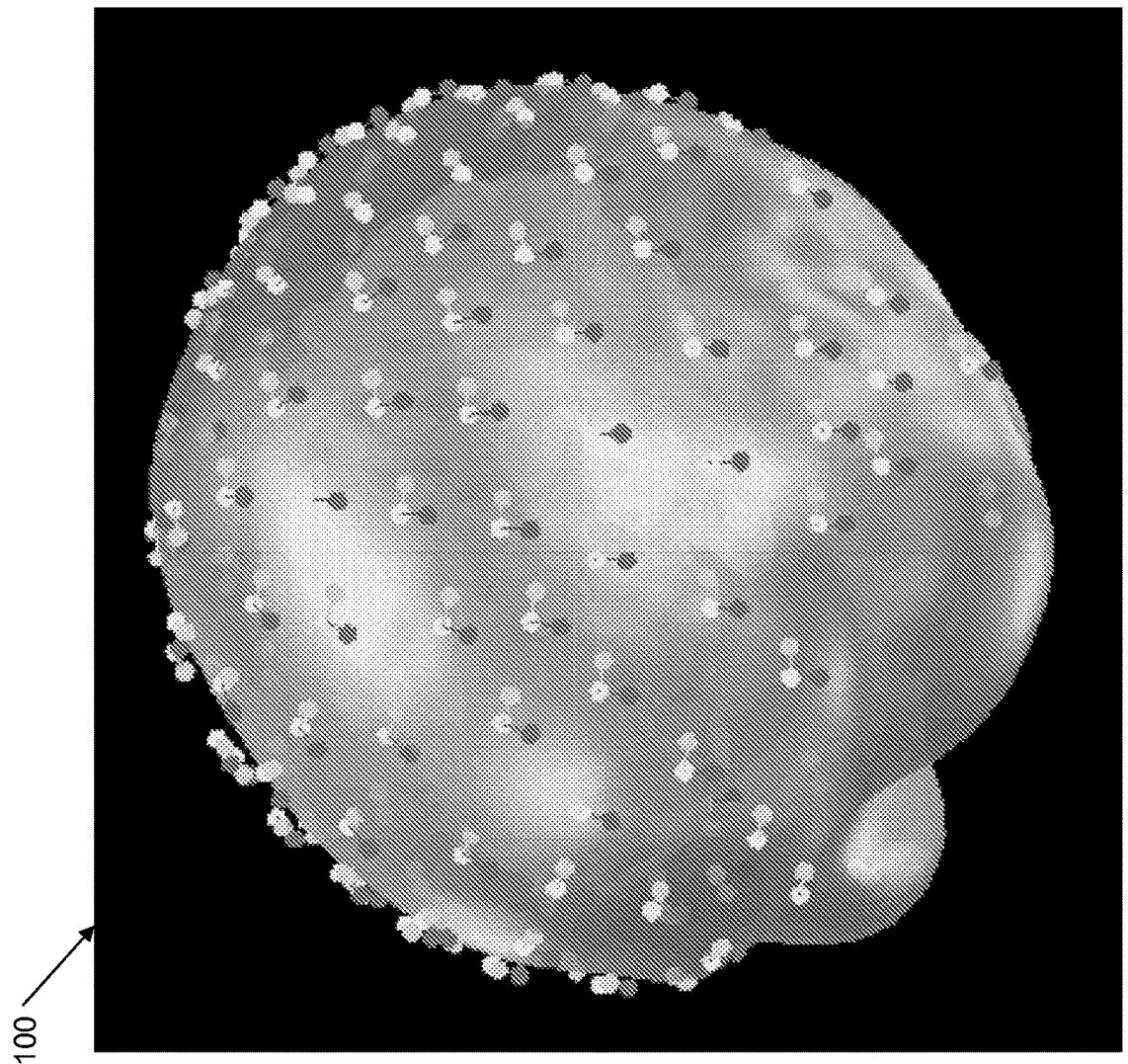
FIG. 1 illustrates tri-polar sensors located on a head, in accordance with some embodiments.

Disclosed herein are methods and apparatuses for the detection and measurement of electric fields associated with brain activity to obtain a real-time, multi-channel image of brain activity is generated. Aspects of the methods disclosed herein comprise measuring a plurality of instantaneous electric field vectors generated by a plurality of electric field sources, the electric field vectors being measured by a plurality of electric field sensors located at a plurality of positions on the exterior of a skull of the subject. An "electric field" is a region of space surrounding charged particles and time-varying magnetic fields. As used herein, an "electric field sensor" is a device capable of sensing an electric field vector. In certain embodiments, the electric field sensors comprise tri-polar or multi-polar electrode sensors. In some embodiments, electro-optical sensors may be used and may be photonic crystals or mach-Zehnder interferometers made of an electro-optic material such as lithium niobate (LiNbO$_3$). In such embodiments, one, two or three components of the electric field are measured.

Aspects of the methods include measuring brain activity in a subject. For instance, the disclosed methods and apparatuses can measure brain activity that is generated from an external stimulus, including auditory, somatosensory, visual, or taste stimuli. In addition, the disclosed methods and apparatuses can measure brain activity generated by neurological conditions such as epilepsy, brain damage caused by seizures or traumatic brain injury, autism, Alzheimer's disease, cancer, and cardiovascular conditions such as stroke. In such embodiments, the methods and apparatuses are useful to diagnose neurological conditions. The disclosed methods and apparatuses are also useful in determining a subject's consciousness, as well as diagnosing injuries. The methods and apparatuses provided herein can also be used to map the brain prior to brain surgery or determine where a surgeon should operate.

The measurement of brain activity can be accomplished by positioning a plurality of electric field sensors at multiple positions on the exterior of a skull of the subject and measuring one to three components of a plurality of instantaneous electric field vectors generated by a plurality of electric field sources, the electric field vectors being measured by the plurality of electric field sensors. In these embodiments, the methods comprise determining brain activity of the subject based on the measurement of the plurality of instantaneous electric field vectors. In certain embodiments, the methods and apparatuses disclosed herein are used to localize brain activity. As explained in greater detailed below, the presently disclosed methods and apparatuses can be used to generate three-dimensional images of a subject's brain electrical activity when the subject is receiving a stimulus or when the subject has suffered a neurological injury. The disclosed methods and apparatuses are also used in measuring human parameters such as fatigue, drowsiness, alertness, responsiveness, and other such parameters. Nevertheless, the methods and apparatuses disclosed herein are not restricted to localization of electric sources and functional brain imaging as discussed in detail in this disclosure. In certain embodiments, the methods and apparatuses disclosed herein are used for neuro-feedback control of external devices. Pure measurement of brain activity, including measurement of any brain activity involving both of tangential and azimuthal components, or all three components, is present in some embodiments.

In other embodiments, the methods comprise estimating a location of each electric field source from data generated from the plurality of electric field sensors, each electric field sensor corresponding to a distinguishable data channel. In certain embodiments, a real-time image of brain activity is generated.

In additional embodiments, the methods disclosed herein comprise diagnosing a brain injury or disease based on the brain activity of a subject. In certain embodiments, the brain activity of the subject is compared to the brain activity of one or more normal subjects. For instance, the brain activities of normal subjects are stored in a database and can be accessed after measuring the brain activity of a subject. The comparison can identify abnormalities in the subject and lead to additional tests to determine the neurological condition causing the abnormal brain activity. In certain instances, the additional testing includes localization of the brain activity to a particular location. In such embodiments, it is possible to identify a disease by localization of brain activities to a position in the brain.

In addition, the methods disclosed herein comprise estimating a location of each electric field source from data generated from the plurality of electric field sensors, each electric field source corresponding to a distinguishable data channel. In particular embodiments, the disclosed methods estimate a three-dimensional location of each electric field source. The methods disclosed herein also use a mathematical model of head electrical characteristics for estimating the three-dimensional location data, which is described in more detail below.

In certain embodiments, the methods allow for measurement of the difference between two electrodes. This can be accomplished by a common or active ground. However, the methods disclosed herein do not necessarily require a reference point, since the disclosed methods record only local signals. This differs from EEG, where a global potential reference is necessary. Also, because electric fields produced by current dipoles are more focused than their potentials, the disclosed methods and apparatuses provide more uncorrelated signals than EEG. In certain embodiments, this is accomplished by placing the electric field sensors either on the scalp or close to it. Such an arrangement results in improvement to source localization precision. In certain embodiments, the electric field sensors are arranged on a non-metallic cap assembly that is designed to be fitted to the head of the subject. In certain embodiments, the cap is made of a soft material such as cloth, nylon, rubber or soft plastic. In other embodiments, the cap is made of a hard plastic material. In such embodiments, the electric field sensors are distributed to allow for detection and measurement of the electric fields.

The disclosure provides a system of measuring the electric fields of the brain to perform the above-disclosed methods. The apparatuses disclosed herein include sets of sensors that can be arranged with close proximity and high density. The sensors can be electrodes used here that are of low noise with silver core material and with Ag/AgCl coating on the surface preventing any DC polarization. This coating prevents the built-in DC polarization at the scalp-electrode interface.

The sensor apparatuses disclosed herein comprise a plurality of electric field sensors configured to measure a plurality of instantaneous electric field vectors, the plurality of electric field sensors are distributed evenly at a plurality of locations on the exterior of a skull of the subject. In these aspects, the instantaneous electric field vectors include at least one of tangential, azimuthal and radial components. In such aspects, the sensor apparatus comprises a computer for processing the measured electric field vectors, the computer comprising at least one processor and a memory providing code to the at least one processor configured to estimate the noisiness of each electric field sensor using data from at least one of the plurality of electric field sensors and identify sources for the measured electric field vectors.

The apparatuses disclosed allow for the detection and measurement of electric fields. In particular embodiments, the sensor apparatus monitors brain activity of a subject. In general, the apparatuses disclosed herein include a plurality of electric field sensors configured to measure a plurality of instantaneous electric field vectors. The plurality of electric field sensors are distributed evenly at a plurality of locations on the exterior of a skull of the subject, the instantaneous electric field vectors including tangential and radial components.

In particular embodiments, the individual electrodes of the multi-polar (2, 3, 4 or more) electrode are spaced approximately 1-10 mm from one another. In additional embodiments, the electrodes are positioned at right angles.

In some embodiments, the multi-polar electrode sensors are made of silver chloride (AgCl). Other materials for making multi-polar sensors include gold, metal alloys, tin, tin-plated metals, copper, gold-plated silver, gold-plated copper, pre-gelled, and foam materials.

In certain instances, the plurality of electric field sensors is at least 128 sensors. In these embodiments, the electric field sensors are spaced such that they are closely paired (e.g., each electric field sensor is spaced approximately 1 cm or less from other electric field sensor). In other embodiments, the electric field sensors are spaced at distances of greater than 1 cm.

In some embodiments, a measurement is conducted without localization of the signals to different parts of the brain. Other embodiments may include a computer for processing the measured electric field vectors. Any computer can be used, including personal computers and tablets, so long as the computer includes at least one processor and a memory providing code to the at least one processor. In some embodiments, the processor is configured to: (i) estimate the noisiness of each electric field sensor using data from at least one of the plurality of electric field sensors, (ii) identify sources for the measured electric field vectors using a source localization technique, (iii) estimate a three-dimensional location for each electric field source from data generated from the plurality of electric field sensors, and (iv) generate a real-time, multi-channel image of brain activity. The algorithms useful in the apparatuses disclosed herein are described in more detail below.

In additional embodiments, the methods and apparatuses disclosed herein use event-related potentials ("ERPs") to improve spatial resolution while reducing the noise levels associated with brain activity. In certain embodiments, each event-related potential is measured and synchronized with time. This is done by providing a stimulus to the subject, such as visual and/or audio stimuli. In such embodiments, from the start of stimulus to the end of it, a measurement of electric field is recorded with the timestamp of the stimulus. Each interval between the beginnings of stimuli is called an epoch. These epochs are averaged over the number of stimulus. Filtering can be done if necessary). The resulting potential differences give the EFEG signal.

Contrary to typical EEG measurements, where the electrode spacings are a few centimeters in separation, the disclosed methods and apparatuses use close proximities (less than 5 mm apart in some embodiments), and small size electrodes (roughly 6 mm in diameter in some embodiments). This configuration allows one to resolve the relative potential differences on the surface of the scalp.

In certain apparatuses, the measurement is run and the continuous signals are recorded simultaneously with stimulation. These events are repeated for ~200 times and the resulting EFEG measurement epochs are averaged.

However, even with the lowest noise systems, that potential difference is still relatively small and buried within environmental and electronic noise. As such, the methods and apparatuses disclosed herein can use visual evoked potentials (VEP) to resolve the net electric potential difference at close proximities.

A major source of noise coming from AC line can couple easily on the subject and the measurement systems. By using differential amplifiers, the common mode noise is highly rejected. This system is superior to capacitive or dry electrodes, since balancing of the electrodes is highly important in minimizing the common noise. In the systems with capacitive pickup electrodes, any triboelectric effect, scalp surface irregularity and low frequency disruptions bring in signal artifacts. In certain embodiments, the methods and apparatuses use conducting gels, as long as the contact is well made, to minimize further these signal artifacts.

In certain embodiments, the apparatuses disclosed herein include instrumentational amplifiers. The instrumentational amplifiers provide low noise, high impedance voltage IC. In certain instances, the IC has laser trimmed resistors built-in. In some embodiments, the apparatuses do not integrate the measured signal, but amplify the differential signal between the electrodes.

In some embodiments, the apparatuses include a ground. The ground can be a common ground. In other embodiments, the ground is an active ground inspired by the driven-right-leg electrode (DRL). In this embodiment, the active ground creates a bias current for the feedback of the amplifier inputs hence increases the common mode rejection of noise.

In certain embodiments, amplification of the electric fields can be accomplished by using differential amplifiers. Differential amplifiers are general names for instrumentational amplifiers. This is the first stage in the circuitry. Differential amplifiers are commonly used for amplifying bio-potentials. A differential amplifier measures the difference between two electrodes. However a bias current is required for the amplifiers to work. This is provided by the common or active ground.

The advantages to the apparatuses disclosed herein relates to the amount of equipment. Such apparatuses do not require as much shielding and bulky equipment as magnetoencephalography (MEG) systems because the electric fields of the brain, although weak, are much stronger than background spurious electric fields than are the magnetic fields generated by the brain compared with background spurious magnetic fields. MEG requires bulky cryogenic equipment and specially constructed magnetically shielded rooms. This makes the methods and apparatuses disclosed herein for EFEG less expensive, and also allows for the positioning of several field sensors in close proximity to the scalp and to each other, which allows for the measurement of several components of the field instead of just one component, as current MEG systems use. Sampling all 3 field components of magnetic field close to the scalp is technically challenging because of the relatively large sizes of the gradiometer coils and the necessity of keeping them inside the full-head dewar. Finally, the disclosed methods and apparatuses for EFEG provide 1 millisecond time resolution. This is superior to functional magnetic resonance imaging (fMRI), which has ~10 second resolution.

Because electric fields produced by current dipoles are more focused than their potentials, the disclosed methods and apparatuses offer significantly more uncorrelated signals than EEG, which results in an improvement to source localization precision.

In some embodiments of the methods described herein, the electric potential and field produced by a current dipole inside a head model including spherical anisotropic shells are derived and are used to estimate the number of uncorrelated signals offered by electric fields of the brain at different distances from the head. Principal component analysis using simulated cortical sources demonstrated that electric fields provide 2-3 times more uncorrelated signals than electric potentials, depending on the distance of the field sensors from the head, and the number of electric field components measured. Source localization simulations for the spherical and BEM head models demonstrated that the localization errors can be reduced two-fold when using electric fields instead of electric potentials.

The disclosed methods and apparatuses further utilize equations for electric fields generated by a dipolar current source in a spherical head model comprising concentric spheres of anisotropic (radial-tangential) conductivity. Electric fields generated near the head surface are shown to be on the order of 1 mV per meter for 10 µV evoked potentials. Simulations using an anisotropic spherical head model as well as an isotropic boundary element head model demonstrated that high-density measurements of electric field on or near the head surface provided 2-3 times more uncorrelated signals of cortical activity than potential measurements at the same locations. Tangential components of electric field (with respect to the scalp) may be more informative than the normal component, and provided slightly more usable signals (signal-to-noise ratio) than the full field for a realistic signal-to-noise range. Accordingly, source localization of simulated cortical sources may be significantly improved when the tangential components of electric field are localized instead of electric potential.

Additionally, the methods and apparatuses disclosed herein can model the distribution of electric fields near the scalp and use this fields for functional brain imaging.

1. Implementation

Currently, no contact-free electric field sensors of sufficient sensitivity are available. Instead, a particular arrangement of the bipolar potential sensors can provide a practical solution to measuring electric fields.

FIG. 1 illustrates tri-polar sensors located on a head in accordance with certain embodiments. 128 sensors are depicted positioned on the human head. The shown sensor locations are typical for high-density EEG and MEG sensor montages—covering the top half of the scalp, avoiding the lower half, where jaw muscles activity makes brain signals too noisy.

Figure 2:
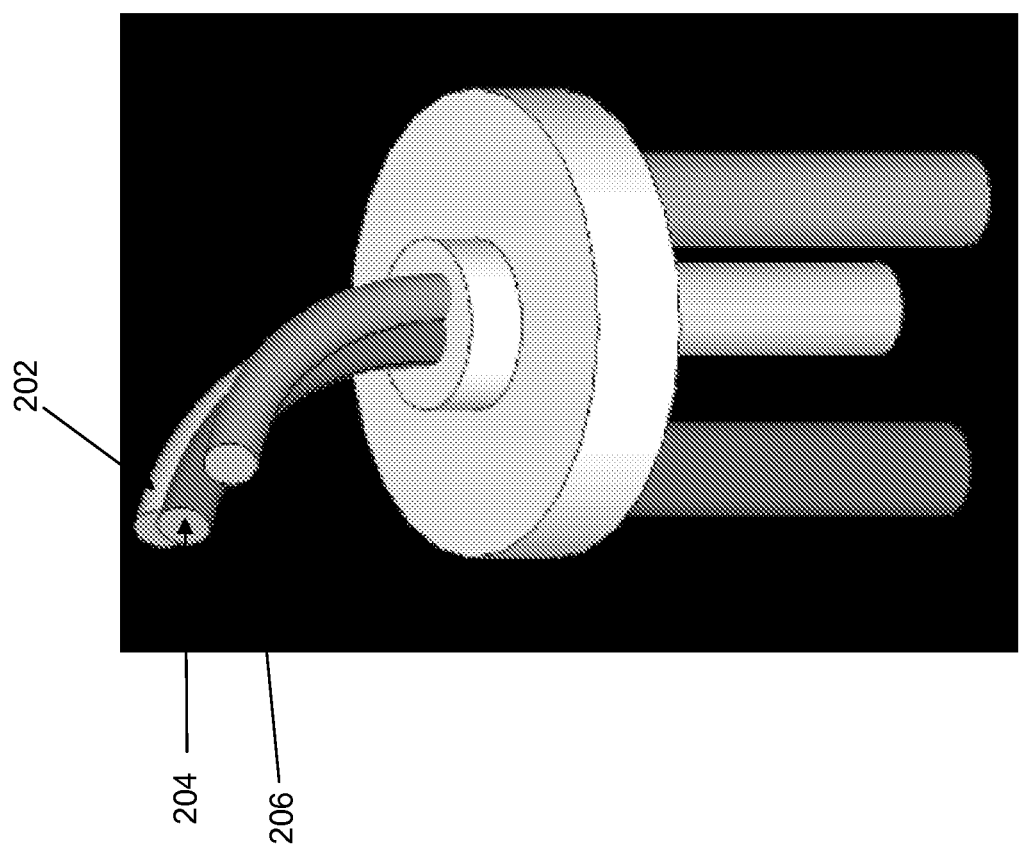
FIG. 2 illustrates the geometry of a tri-polar sensor, in accordance with some embodiments.

FIG. 2 illustrates the geometry of a tri-polar sensor in accordance with certain embodiments. The 3 tri-polar electrodes are: reference 202, inclinational 204, and azimuthal 206. The reference-inclinational and reference-azimuthal pairs are orthogonal to each other and sample the corresponding components of electric field along the scalp.

The two tangential components of the field may be measured by a triplet of spaced (e.g., 5-10 mm) EEG electrodes positioned at a right angle and forming a 'tri-polar' electric field sensor (FIG. 2). Because electric field is given by the negative gradient of the electric potential, difference of potentials between the reference electrode (shown in yellow) and the two other electrodes (inclinational and azimuthal) may be approximating the corresponding electric field components. Placing the reference electrode of each sensor in close proximity to the remaining two electrodes reduces external noise in the resulting electric field measurement compared to the conventional EEG measurements, where one or two distant reference electrodes are used instead.

Because direct electric contacts between the three 'tri-polar' electrodes should be precluded in certain embodiments, and because the distances between the electrodes may be small, it is preferable not to use the electrolyte or conductive gel usually used with EEG sensors. Instead, these reasons suggest the use of 'dry' electrodes. The concept of dry EEG electrodes was recently successfully introduced on the market by g.Tec Medical Engineering. 'Dry' electrodes may be highly applicable to EFEG measurements, where the quality of electric contact between the electrodes and the scalp is less critical than for EEG due to near-cancellation of external noise by the use of the closely positioned reference electrode in each sensor.

The tri-polar sensor can consist of three golden pin electrodes 2-3 mm in diameter and 10-15 mm long attached to a plastic disk (FIG. 2), in accordance with certain embodiments. This geometry allows for easy reach to the scalp even through thick hair, which is problematic using conventional electrolyte or gel-loaded EEG electrodes due to their large area. 100-200 tri-polar EFEG sensors may be pressed to the scalp either by an action of an elastic cap or by a spring action when spring-loaded and attached to a hard-shell helmet (FIG. 1). Using only three pin electrodes in each sensor provides a potential solution to the problem of putting each electrode in electric contact with the skin: at least three contact points may be used to balance an object on a surface.

Figure 3:
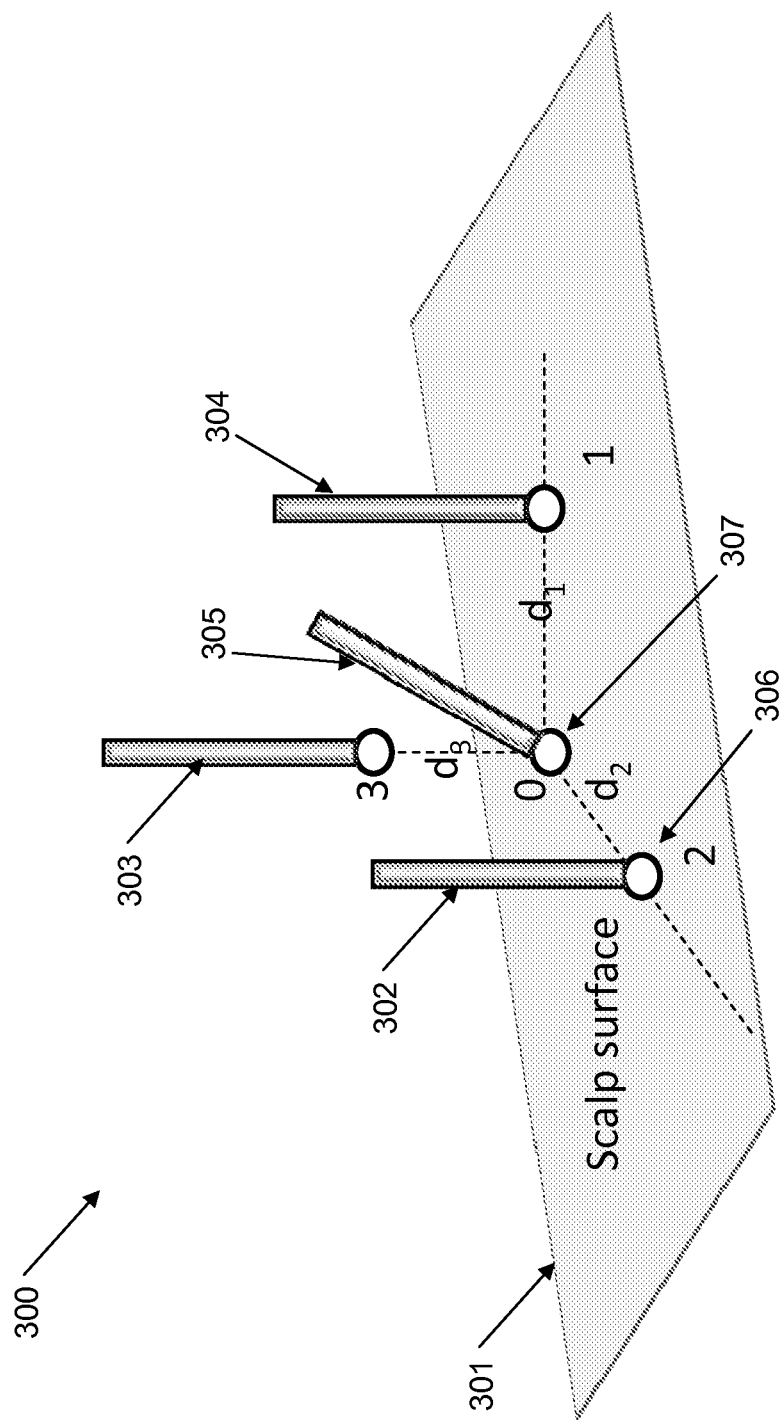
FIG. 3 illustrates the arrangement of a tri-polar electrode array on and above a body, in accordance with some embodiments.

FIG. 3 illustrates the arrangement of a tri-polar electrode array on and above a body, in accordance with some embodiments. Arrangement 300 depicts three electrodes 302, 303, and 304 on or above scalp surface 301. Electrodes 302 and 304 are located on scalp surface 301, making contact at, e.g., contact point 306; electrode 303 is located above scalp surface 301. The depicted electrode configuration is for measuring three potentials $V_i$, such that all three components $E_i$ of the electric field, $E_i=(V_i-V_0)/d_i$, i=1,2,3 may be calculated from the potentials. Using electrodes 302, 303, 304 to measure the three components allows for computing the electric field at point 307. Reference electrode 305 is in contact with the scalp at point 307 and provides a reference potential. As well, a tangential, inclinational, and azimuthal component of the electric field may be measured using this technique.

1.1. Implementation of Electrodes

Grass brand Ag/AgCl coated electrodes (F-E6SHC) may be used in certain embodiments. These are smaller than conventional electrodes. (Typically ~5 mm). The core is silver metal. Ag/AgCl coating has been shown that it makes a quiet skin/electrode interface especially at DC level measurements. This has reduced the first level noise at skin level and taken care of DC components in the noise. We are also using the gel which reduces the skin-electrode impedance to 5 kOhms which is less than the Mega Ohms of impedance if the gel is not used. Lowering the skin-electrode impedance helps with the Nyquist noise reduction, which is proportional to the square root of impedance.

FIGS. 4(a)-4(d) illustrate electrode geometries, in accordance with some embodiments. In the following description, "bipolar" indicates that the signal swings above and below a reference point; "DRL" refers to the bias current path which can be actively driven, not necessarily analog ground; "REF" refers to the reference electrode where one electrode from each bipolar input is overlapped; and En refers to an electrode indexed with respect to the reference electrode.

Figure 4:
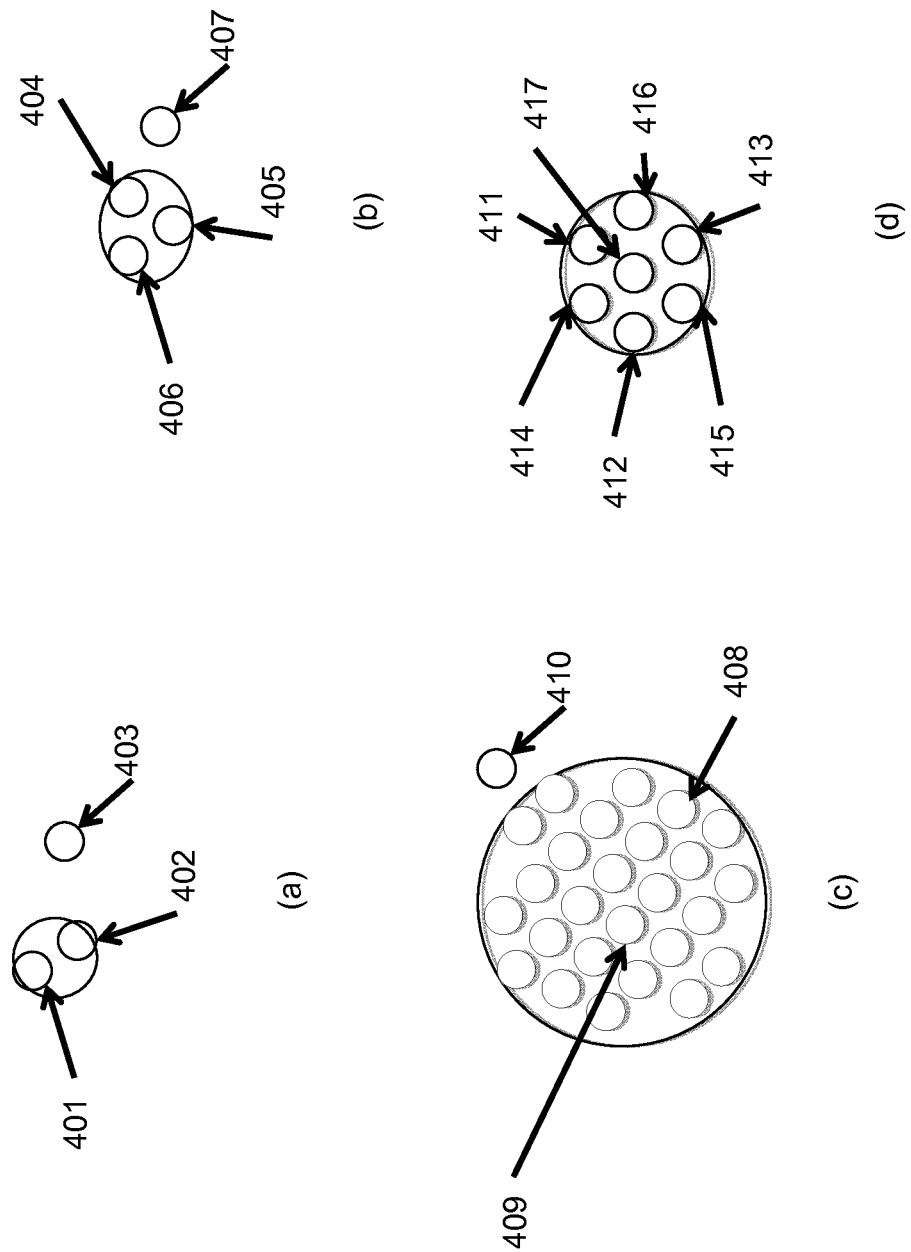
FIGS. 4(a)-4(d) illustrate electrode geometries, in accordance with some embodiments.

In FIG. 4(a), one bipolar electrode (resolves 1D E-field) is shown. Reference electrode 401 is paired with electrode E1 402. Actively-driven bias current path DRL 403 is also provided.

In FIG. 4(b), two bipolar electrodes (resolves 2D E-field) are shown. Reference electrode 406 is paired with electrodes E1 404 and E2 405, and bias current path DRL 407 is also provided.

In FIG. 4(c), multiple bipolar electrodes (resolves 2D E-field for many points) are shown. Reference electrode 409 is paired with several electrodes; an exemplary electrode En is identified as 408. A single bias current path 410 is also provided.

In FIG. 4(d), multiple bipolar electrodes with independent references are shown. Electrodes E1 411, E2 412, and E3 413 are paired with reference electrodes REF1 414, REF2 415, and REF 416. Bias current path DRL 417 is provided in the middle of the electrode bundle.

Figure 5:
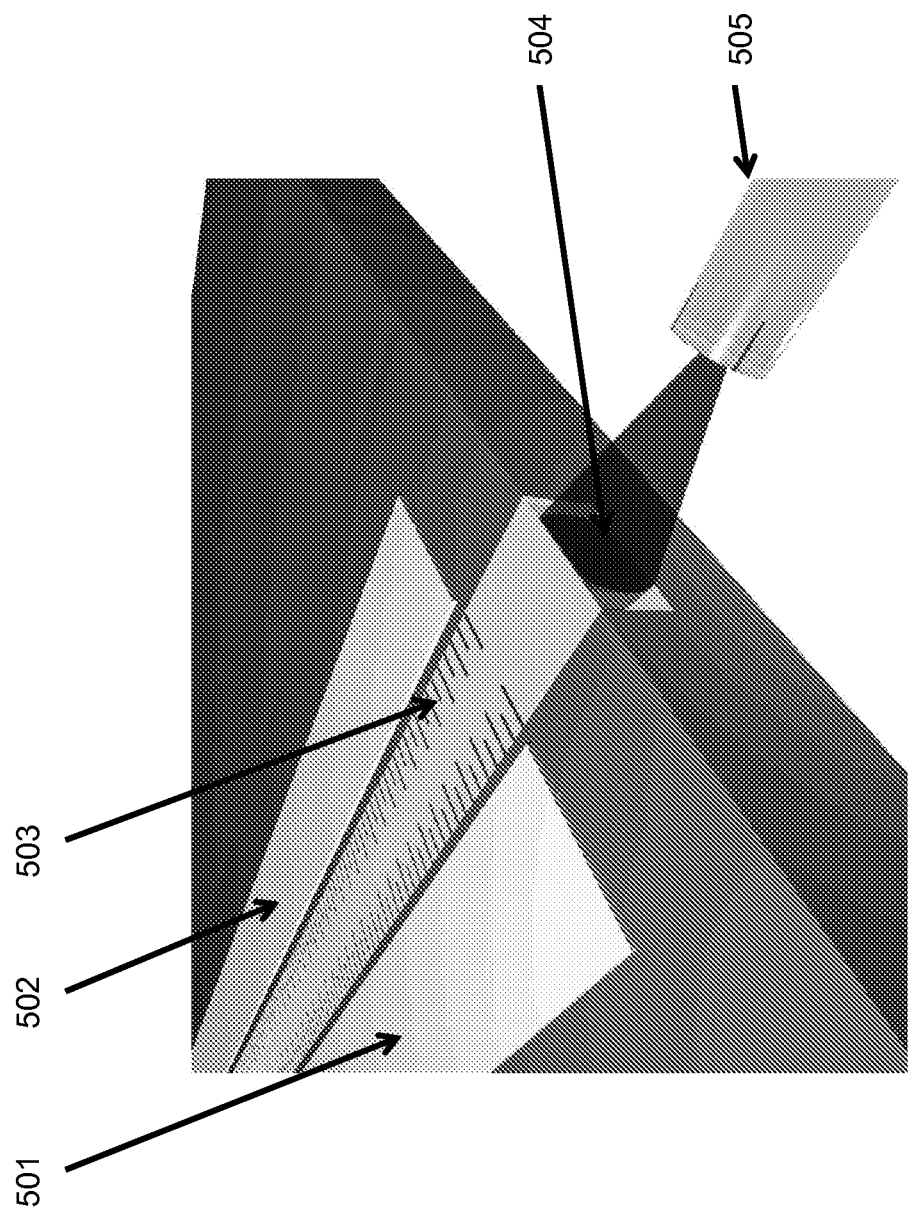
FIG. 5 illustrates a lithium niobate electro-optical electric field sensor, in accordance with some embodiments.

FIG. 5 illustrates a lithium niobate electro-optical electric field sensor, in accordance with some embodiments. Lithium Niobate is an electro-optical material. In the presence of an electric field, electrodes 501 and 502 couple to that field and direct it to the optical waveguide with a photonic crystal 503. The photonic crystal inside the waveguide creates band-pass or band-stop. The electric field is measured as an amplitude change at the output 504 using an optical fiber 505.

Figure 6:
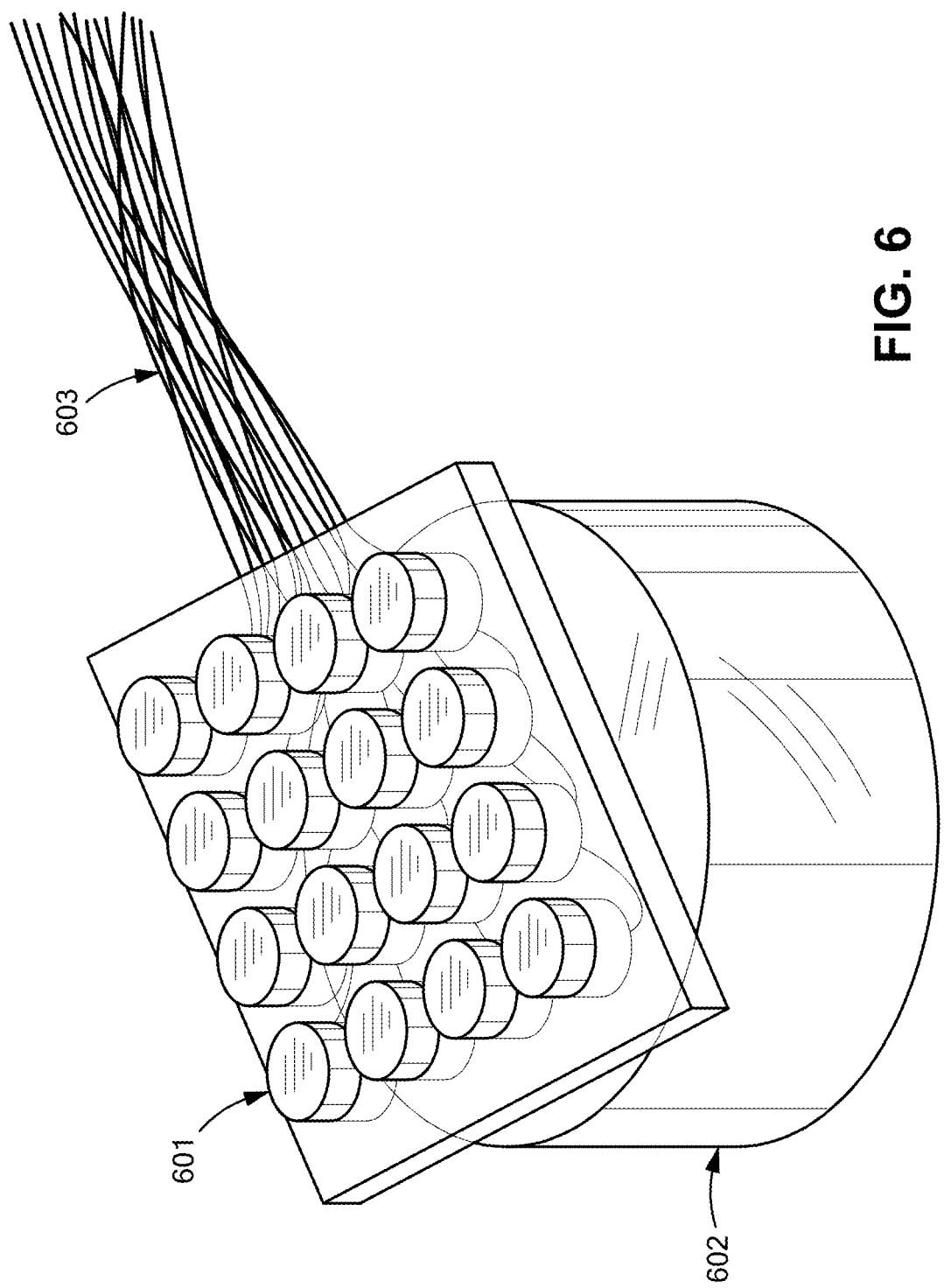
FIG. 6 illustrates copper electrodes in a polydimethylsiloxane (PDMS) mold, in accordance with some embodiments.

FIG. 6 illustrates copper electrodes 601 in a polydimethylsiloxane (PDMS) mold, in accordance with some embodiments. Wires 603 connect the electrodes to the measurement apparatus. The mold 602 is a transparent piece of polydimethylsiloxane (PDMS). PDMS molds can be custom-made easily depending on various head shapes and electrode geometries. Since PDMS is a transparent material, it allows for visualization of the electrodes during head positioning. The rigidity/flexibility of PDMS mold can be adjusted by changing the mixing ratio. PDMS is shown to be a very stable material, and suitable for bio-applications.

Figure 7:
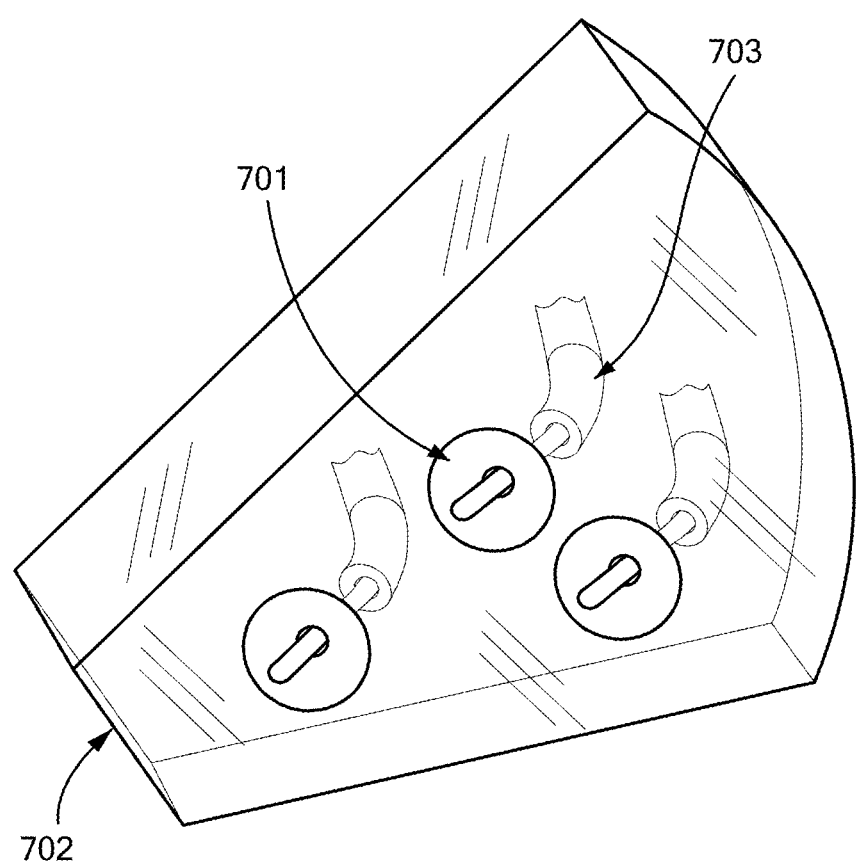
FIG. 7 illustrates silver electrodes in a PDMS mold, in accordance with some embodiments.

FIG. 7 illustrates silver electrodes 701 in a PDMS mold 702 connected via wires 703 to a measurement apparatus, in accordance with some embodiments. The electrodes may be silver or silver chloride.

Figure 8B:
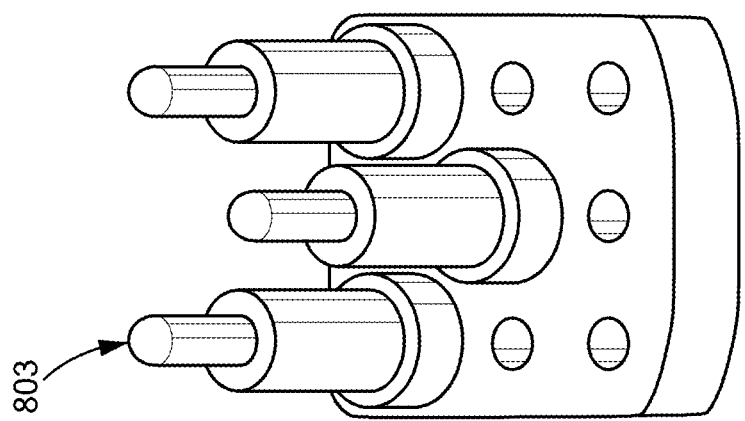
FIGS. 8(a)-8(b) illustrate spring-loaded electrodes in a PDMS mold, in accordance with some embodiments.
Figure 8A:
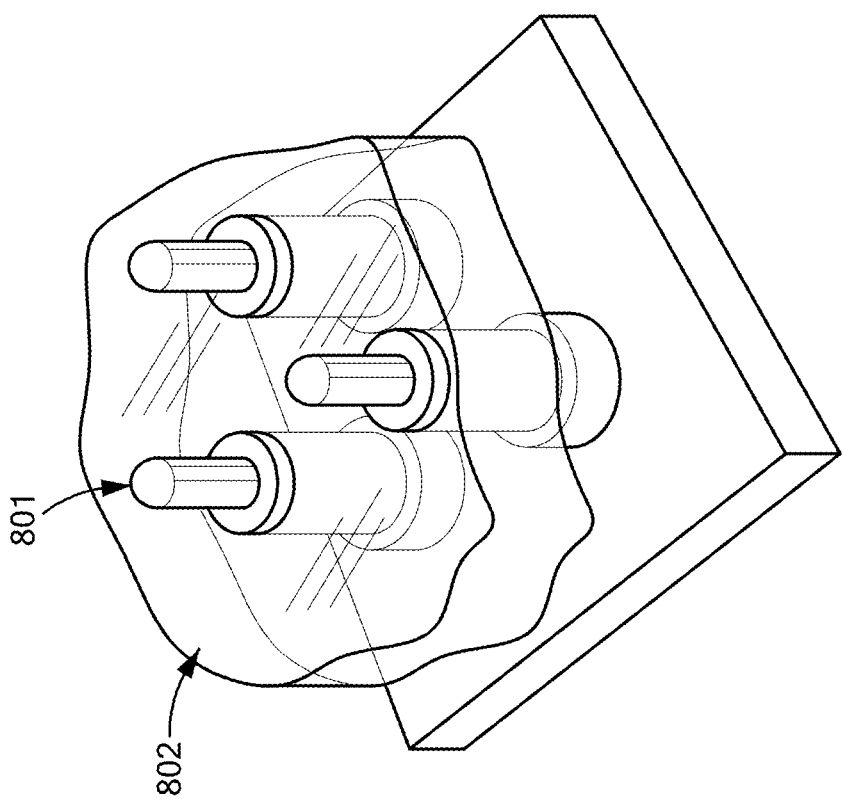

FIGS. 8(a)-8(b) illustrate spring-loaded electrodes 801, 803 in a PDMS mold 802, in accordance with some embodiments. The electrodes depicted here are copper-alloy pin electrodes. The spring-loaded electrode geometry is further described below.

Figure 9B:
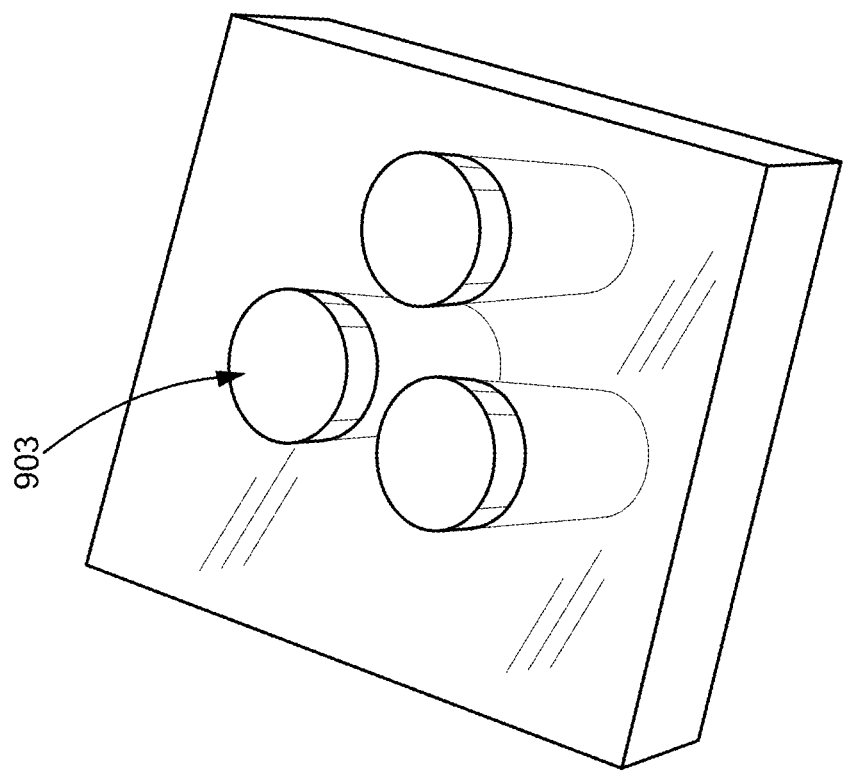
FIGS. 9(a)-9(b) illustrate silver-in-copper electrodes in a PDMS mold, in accordance with some embodiments.
Figure 9A:
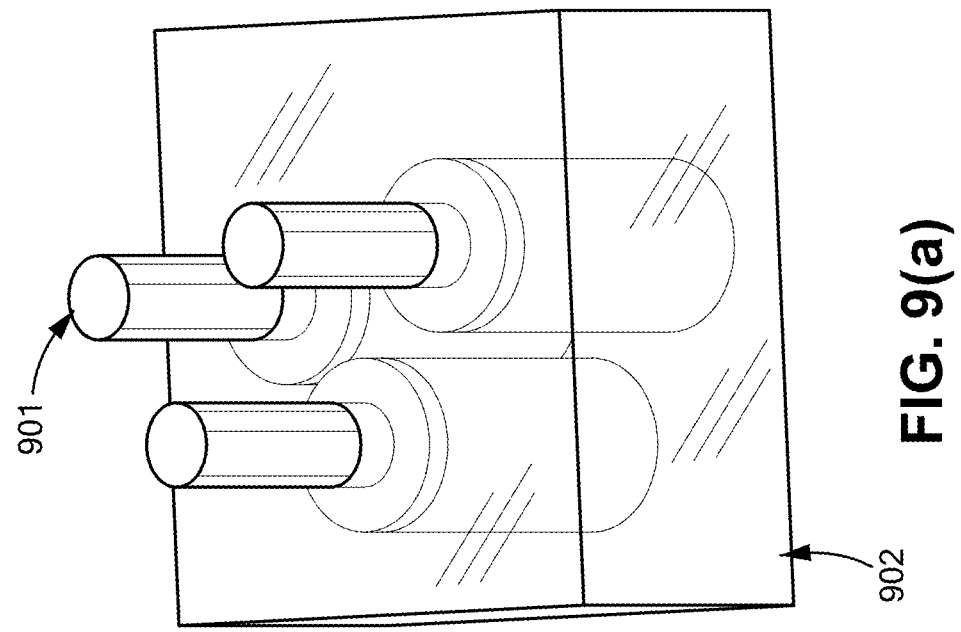

FIGS. 9(a)-9(b) illustrate silver-in-copper electrodes 901, 903 in a PDMS mold 902, in accordance with some embodiments.

Figure 10:
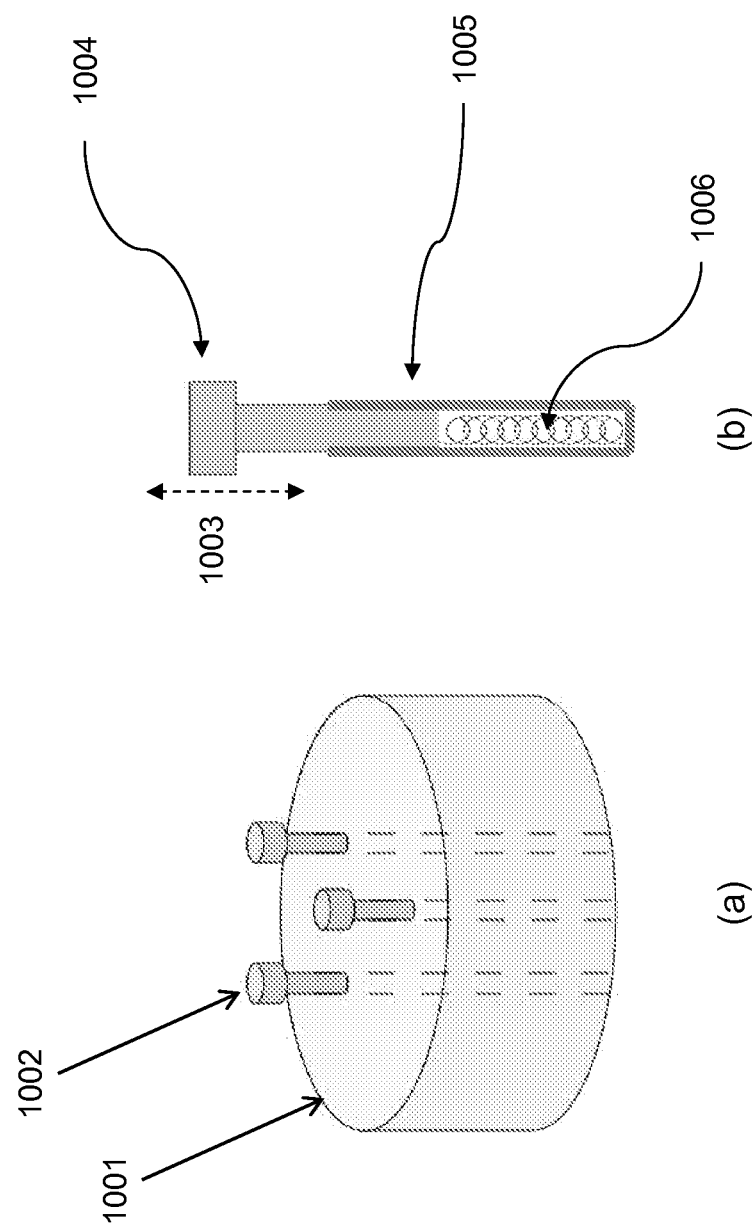
FIGS. 10(a)-10(b) show a schematic view of spring-loaded electrodes in a PDMS mold, in accordance with some embodiments.

FIGS. 10(a)-10(b) show a schematic view of spring-loaded electrodes 1002 in a PDMS mold 1001, in accordance with some embodiments. Spring loaded electrodes 1002 have advantages over the standard cup shapes. The spring loaded electrodes provide constant pressure on the head so that they do not come off the head as easily. The pressure can be adjusted depending on the selection of the electrodes with different spring constants. The initial spring forces can be from 2-7 oz to 5-19 oz (working travel). The material can be Ag/AgCl or gold coated brass, copper, etc. The electrodes can be molded in various geometries based on the electrode design. Electrode 1002 is represented schematically in FIG. 10(*b*). Electrode tip 1004 sits within electrode sheath 1005, which also contains spring 1006. The action of the spring 1006 and the constraining sheath 1005 provides for linear motion of electrode tip 1004, enabling the tip to sit on the scalp of the subject. Arrow 1003 represents the range of travel of the spring-loaded electrode tip 1004.

Figure 11:
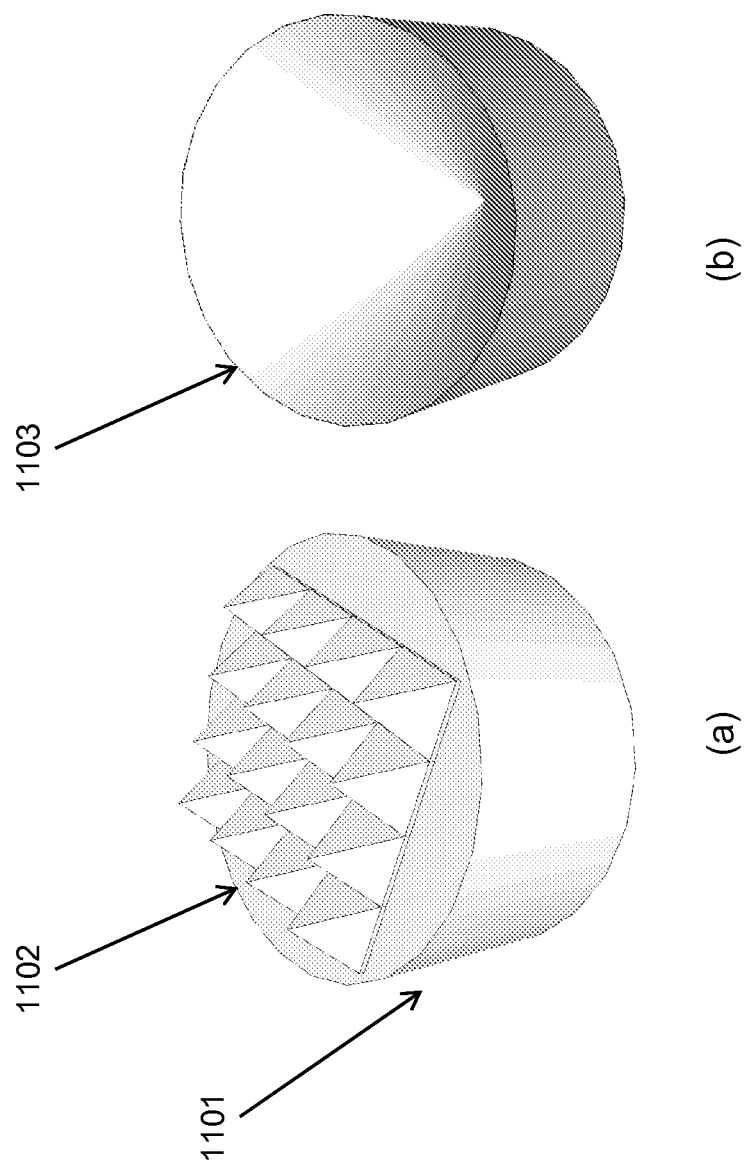
FIGS. 11(a)-11(b) show electrode tip designs, in accordance with some embodiments.

FIGS. 11(*a*)-11(*b*) show electrode tip designs, in accordance with some embodiments. Electrode tip 1102 sits on electrode base 1101. The electrodes can have various tip designs. A cup-shaped tip 1103 is ideal since it can hold electrode gel, and because the rim makes better contact when it is moved over the head; the rim is able to go through hair and provides a better skin-electrode interface. A "waffle" tip 1102 typically has a larger surface. The waffle surface holds the electrode gel in that interface and the little pyramids prevent multiple channels from one electrode to the skin resulting in enhanced conduction. Both tip types can provide a gentle exfoliating effect when moved around the scalp, which can significantly reduce the electrode-scalp interface impedance.

Figure 12:
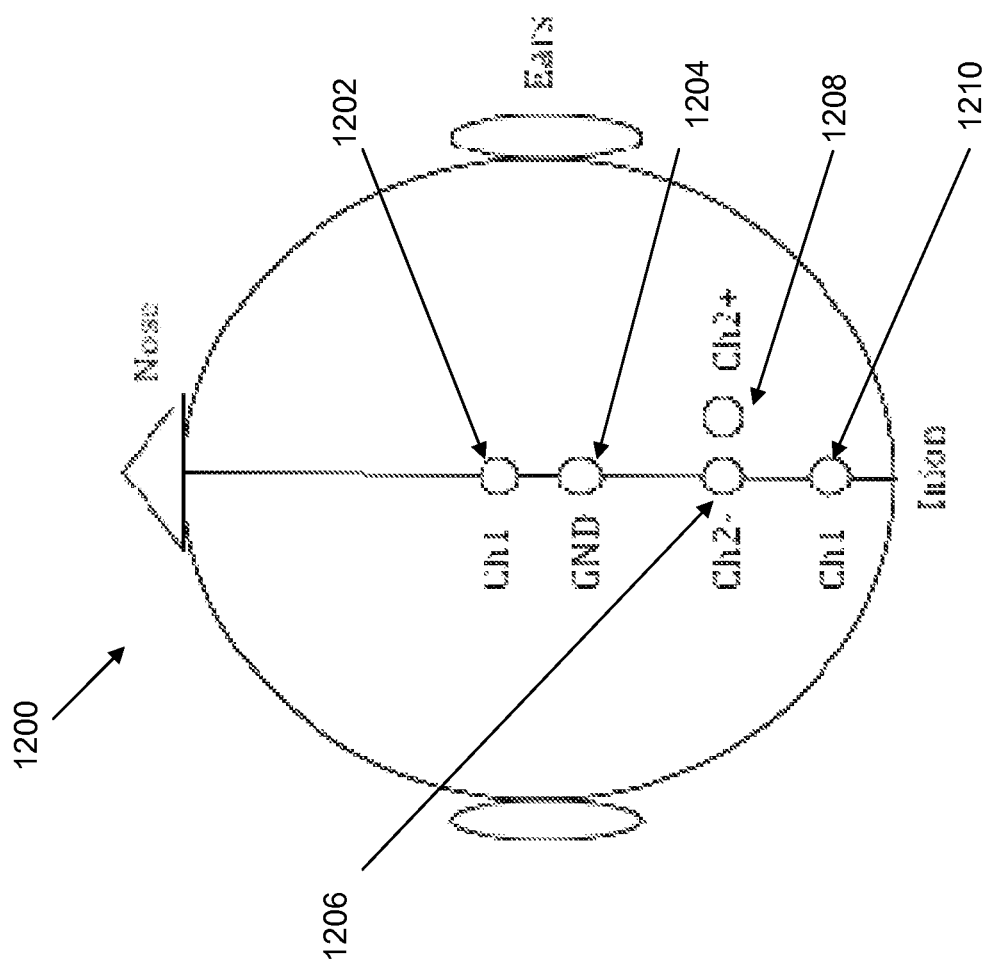
FIG. 12 illustrates a head electrode map, in accordance with some embodiments.

FIG. 12 depicts an electrode mapping on the head showing EEG and EFEG electrode placement, in accordance with certain embodiments. Ch1 electrodes 1202, 1210 and Ch2 electrodes 1206, 1208 are connected to GND electrode 1204. In conjunction with GND 1204, Ch2− 1206 and Ch+ 1208 electrodes provide two signals corresponding to two tangential electric field components. We have made the separation as close as possible (Ch2 electrodes in FIG. 12), down to the minimum separation level which is less than 0.5 cm apart. We have started with regular separation distances (a few centimeters apart) and we were still able to measure at sub cm distances. In these measurements, EEG corresponds to Ch1 electrode placement and EFEG corresponds to Ch2 placement where the distance could be reduced as much as possible. Therefore the signal amplitude for EFEG would be smaller as compared to EEG signal as expected.

Bipolar electrode setup with an active ground electrode can be used and have been used in specific embodiments. In order for the circuitry to reject common mode noise, the current has to have a path for return which is through active electrode. The active electrode (as shown in designs) has an elevated potential. So overall our electrode system for one channel has 3 electrodes.

1.2. Data Acquisition

Figure 13:
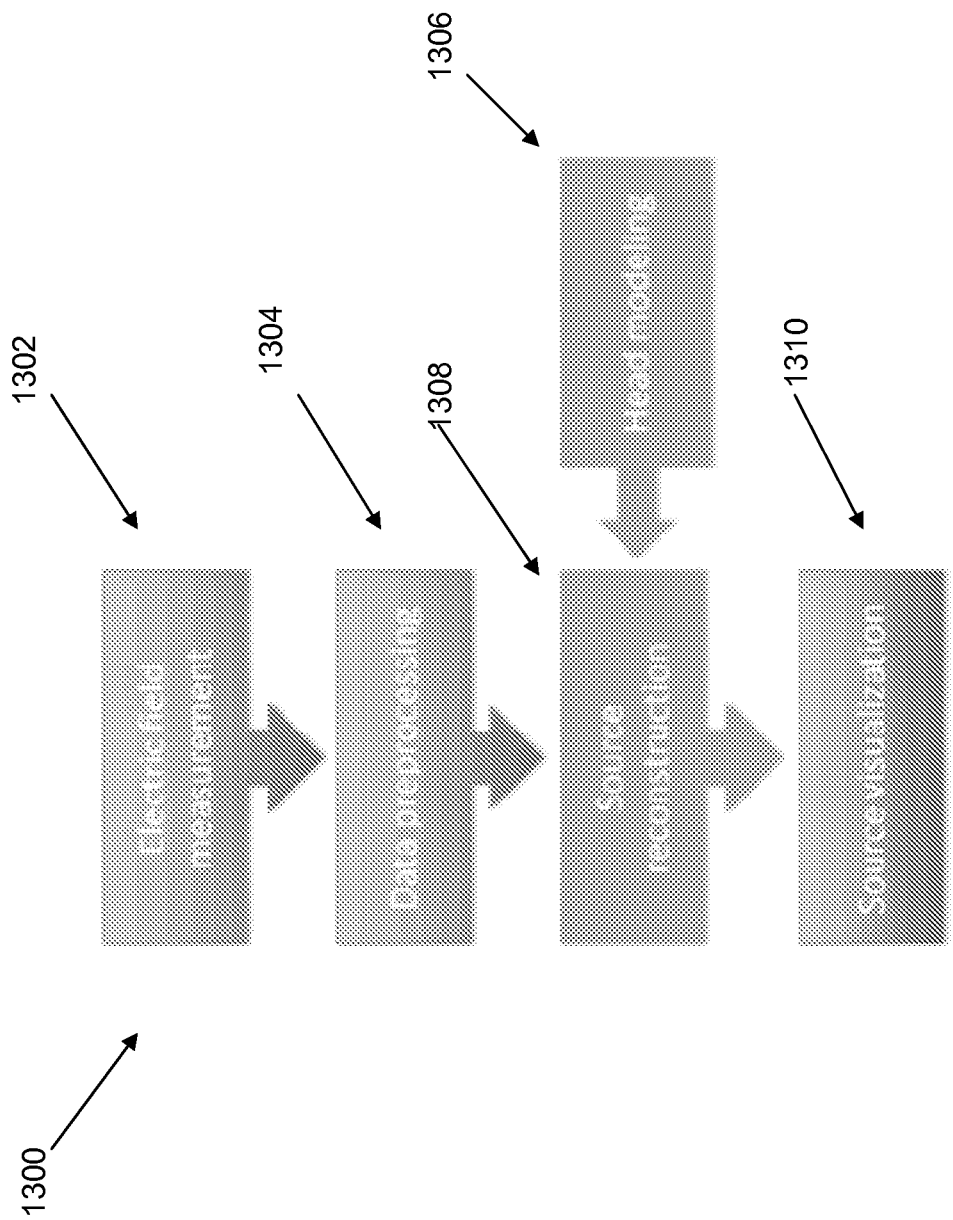
FIG. 13 illustrates a process flow chart, in accordance with some embodiments.

FIG. 13 is a flow chart showing steps performed in the process of measurement and data acquisition, in accordance with certain embodiments. Flowchart 1300 shows electric field measurement at step 1302. The measured data is then preprocessed at step 1304, the preprocessing step includes muscle activity artifact and amplifier artifact rejections, replacement of noisy channels and, finally, data averaging. The preprocessed data is then combined with a head model generated at step 1306 to obtain the forward solution. The forward solution is used to localize the sources of the EFEG at step 1308. Step 1308 is also called source reconstruction. At step 1310, the source data is visualized.

Regarding measurement step 1302, the potential measurements are acquired. After the electrodes are mounted on the head (using the conductive gel) of a subject, the amplification and the signal can be measured on the screen in real-time to compare the noise levels. A power spectrum plot showing the FFT distribution of the signals may also be helpful. Typically a noise level of 60 Hz AC line with −30 dB is satisfactory for a good measurement. If the noise level is more, saturation of the amplifier may result, reducing signal quality. It can be possible to filter the data later on using software but in this case the signal quality and details in the data would be lost. So the best practice may be to measure with the least amount of noise coupling. The power spectrum also helps to see the other noise sources if there are harmonics of the AC line.

It is also possible to electrically isolate the acquisition setup from the AC line. Such electrical isolation is well known in the art.

Electrical isolation as to the measurement path reduces AC noise. A simple approach would be reducing the impedance path and hence the capacitive coupling is reduced. The shorter the distance between the electrodes and the electronics, the better the noise quality due to the reduced potential difference coming from the capacitive coupling.

In another embodiment, wireless data transmission may be used between the sensors and the computer associated with the apparatus or any other processor. This is allowed due to the noise being even lower due to these practices listed above. Also the mobility to the system may be enhanced. Zigbee (Xbee) modules may be used for the data transmission. These small programmable modules can transmit information using their own communication protocol (Bluetooth or 802.11 or 802.15 WiFi). The signal power levels are also adjustable from −7 dBm to +3 dBm. The data transmission rate can go up to at least ~300 kBbps. An Arduino board may be used to capture the analog channel data. The Arduino has its own built-in analog-to-digital (ADC) port and converts the data to a digital signal that Zigbee can process.

Bipolar electrodes may also help to reduce noise. This is due to the reduced impedance path. Since the path is smaller there is less capacitive potential build-up. However, as far as the EFEG measurements, this also reduces the amount of signal between the electrodes.

For the data acquisition, an USB-6008 may be used, which is a data acquisition (DAQ) board from National Instruments. The differential inputs per channel may be used to record and see the data on the screen. A laptop running a signal acquisition program, such as SignalExpress, may be used to observe and record data in real time. A typical recording time is 5 minutes per session.

Figure 14:
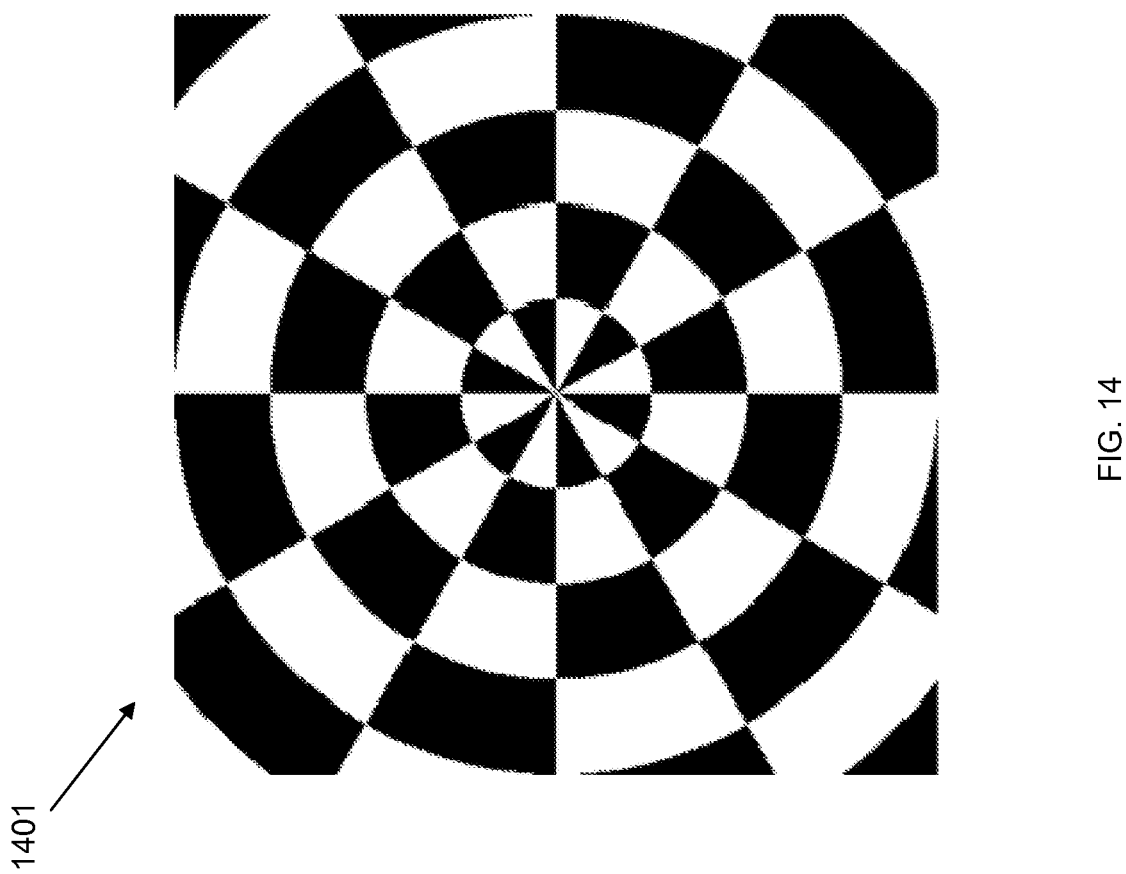
FIG. 14 illustrates a circular checkerboard to be used, in accordance with some embodiments.

FIG. 14 is a depiction of a checkerboard pattern 1401, in accordance with some embodiments. During recording, a circular checkerboard pattern changes every second on the screen of a laptop computer. At the corner of the screen, a square region flashes and this inputs an analog signal for the photodiode. This signal is the timing signal for the checkerboard. Each measurement session is divided into smaller subsections so that the subject has time to blink in between these subsections. Another computer is recording the data during the checkerboard pattern flickering.

The photodiode allows for triggering of the signal with the image change. In the event that a separate screen/monitor is used to change the image, the photodiode gives feedback to the DAQ. However, systems that do not require a photodiode may also be used. For instance, a host computer may change the image on the display and record data continuously when the image is triggered, without a photodiode.

The photodiode is biased, and this potential is fed into one of the analog channels of the DAQ board. The typical level of photodiode signal is −100 mV (depending on the display brightness). The signal coming from the electrodes is amplified 20,000 times. In real-time, the signal is displayed on the screen and the amplified signal can be 1 Vpp. In order to use the best signal to digital noise range, the DAQ board can be adjusted such that the differential inputs are from +1V to −1V range, rather than +/−10V range. This reduces the digital noise coming from the bit resolution. If the signal coming from the amplifier circuit doesn't saturate, this indicates a good skin-electrode interface. When the subject who is going through the measurement grinds the teeth or blinks, this would show up on the amplifier screen.

Figure 15:
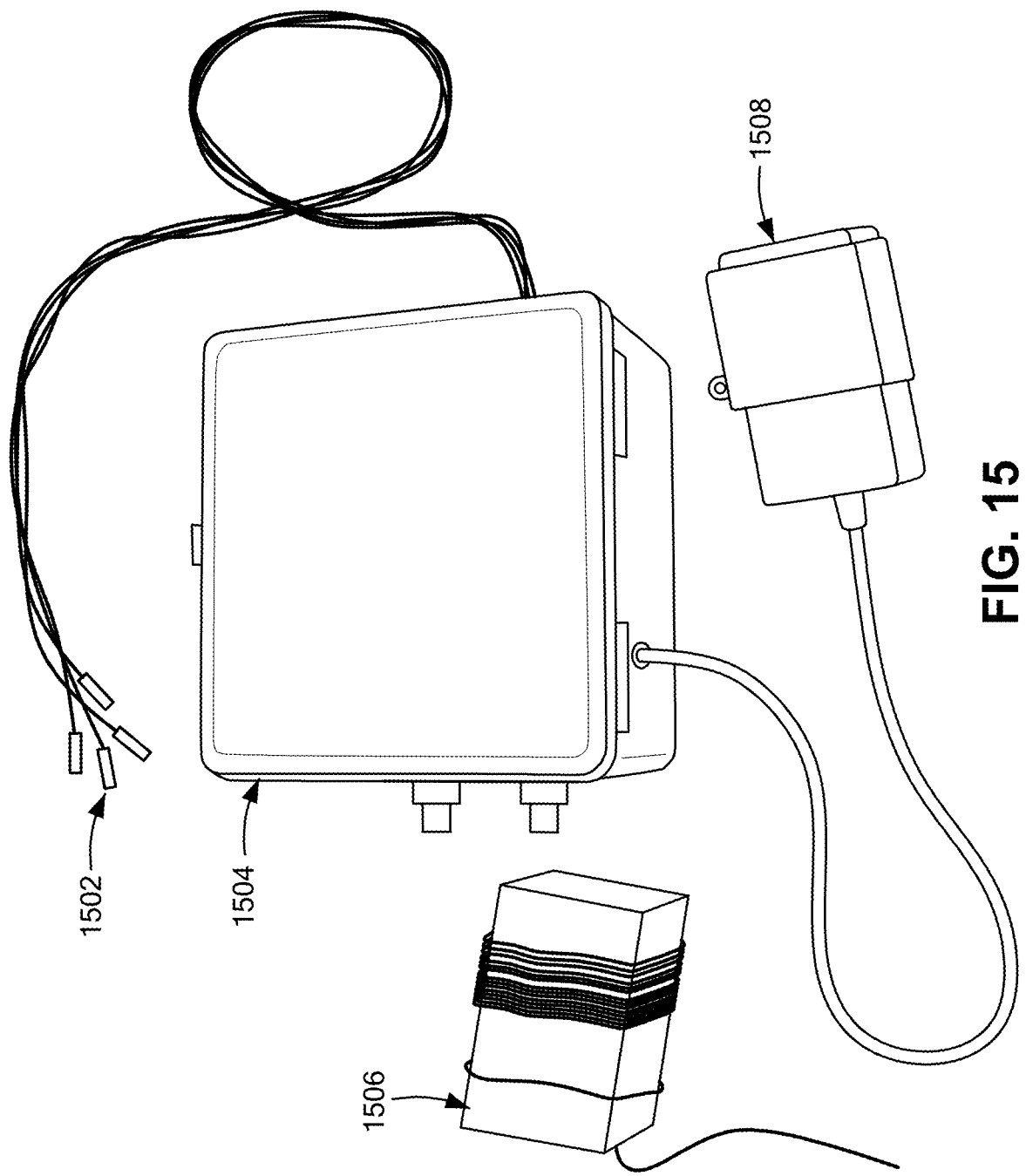
FIG. 15 illustrates a measurement setup, in accordance with some embodiments.

FIG. 15 is a diagram depicting an apparatus as disclosed herein. The apparatus includes silver electrodes 1502, a "lunch box" including circuitry 1504. In certain embodiments, the circuitry receives and sends the signal to a computer (not shown). In other embodiments, the circuitry includes a processor with programming to receive and process data. Such processing includes sending the data to a computer or storing the information in memory on the "lunch box." In addition, processing can include normalizing the data against baseline data from the subject that was taken prior to testing. Furthermore, the apparatus in FIG. 15 includes photodiode 1506 and the USB-6008 DAQ 1508. The photodiode 1506 may be a commonly-available BPW34 photodiode.

The apparatus also includes two-channels. In the apparatus of FIG. 15, an amplification system is used. The amplification is calibrated for both channels using a signal generator and an oscilloscope. The polarities of the electrodes are also matched so that when one channel is recording a peak the other channel is also recording the peak at the same phase and amplitude. Overall, the circuit has high pass and low pass filtering (FIG. 12). That means the levels of the voltages are slightly different at different frequencies. The band pass filter allows the region to pass between DC and 100 Hz (approximately). In the first stage of the circuit, the instrumentation amplifier amplifies the signal up to 10 times and the output is DC filtered. This is required so that the first stage is not saturated by noise. The second stage consists of amplification (typically 2000 times) with a low pass filter built in. The output is directly fed into the DAQ setup.

Figure 16:
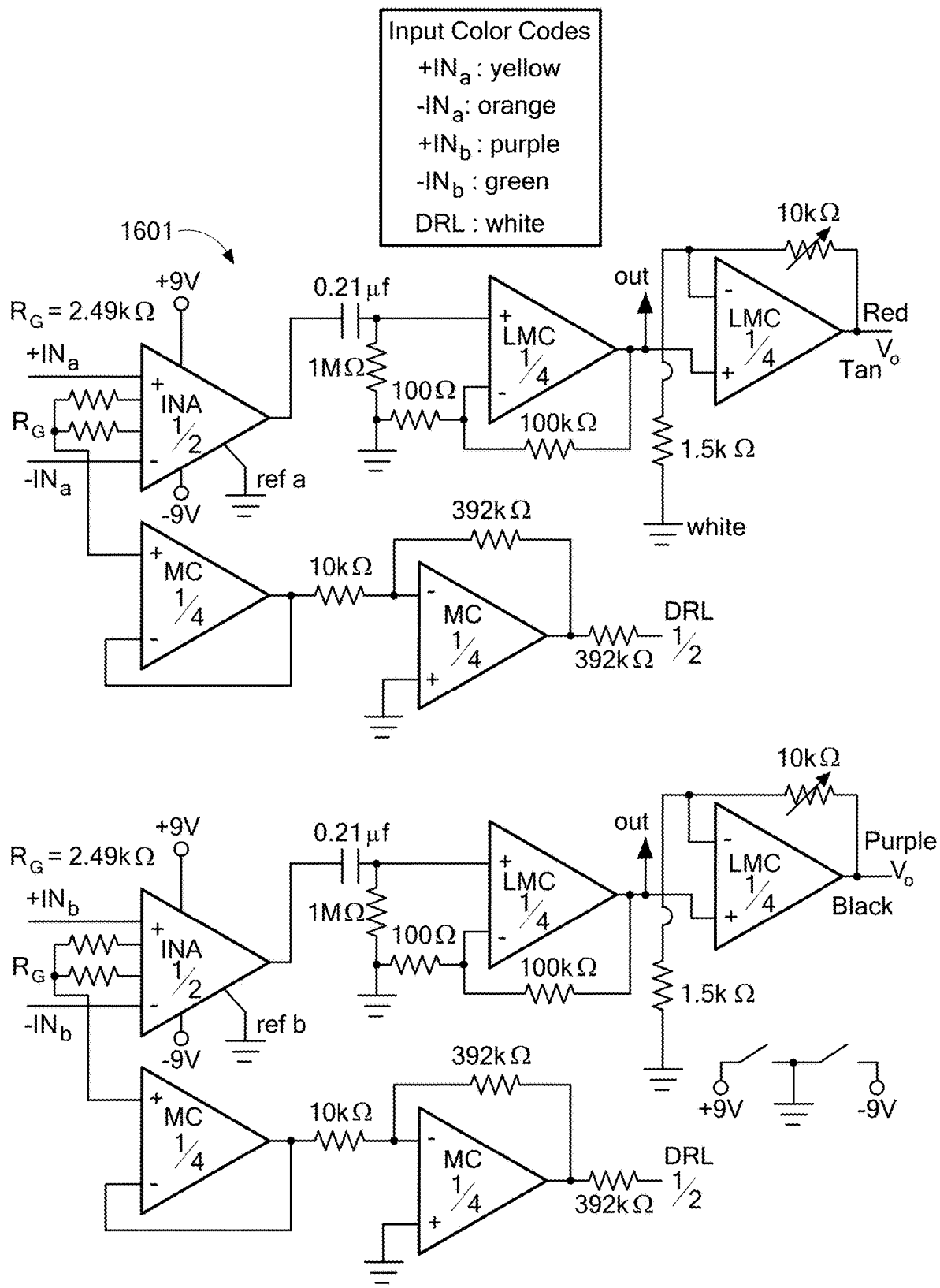
FIG. 16 illustrates an amplifier circuit, in accordance with some embodiments.

FIG. 16 is a schematic diagram for an amplifier 1601, in accordance with certain embodiments. This amplifier may be used in the apparatuses (such as the apparatus shown in FIG. 6) described herein. The sampling rate may be 1 kHz, which corresponds to a 1 ms time interval between each data point.

1.3. Measurements and Data Interpretation

The data is analyzed for each epoch frame. The timing signal is used to identify the starting sequence of each window. This is the photodiode's response to the "on-off" periods of the LCD. The flash of light or the flickering checker-board pattern creates the image on the eyes of the subject and takes around 60-80 ms for the visual signal to arrive as an electrical potential at the back of the head. This shows up as a latency of first peak in the epoch measurements.

Figure 17A:
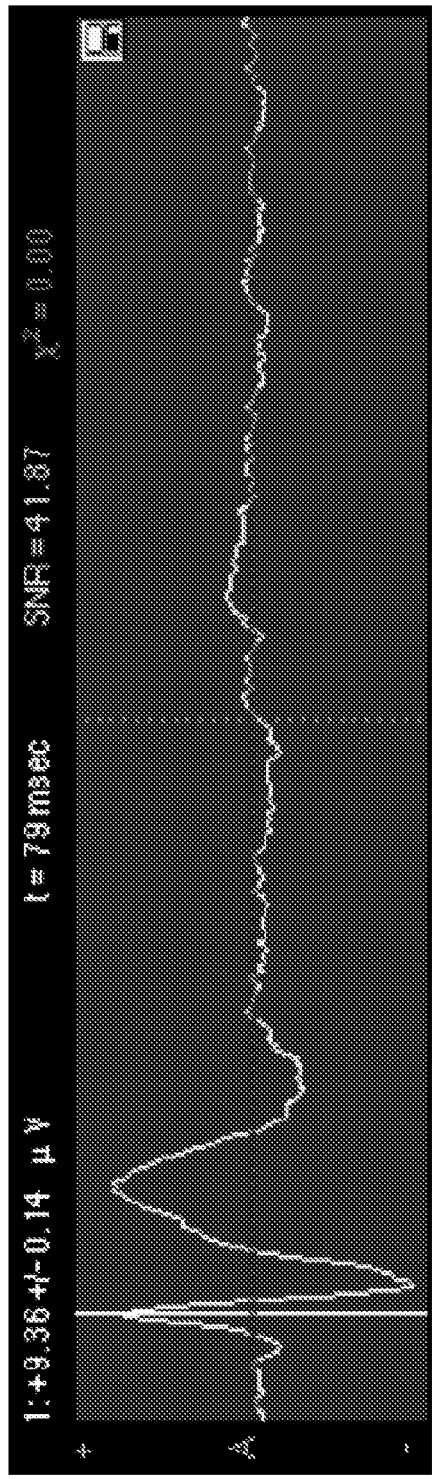
FIG. 17 illustrates EEG and EFEG measurements, in accordance with some embodiments.
Figure 17B:
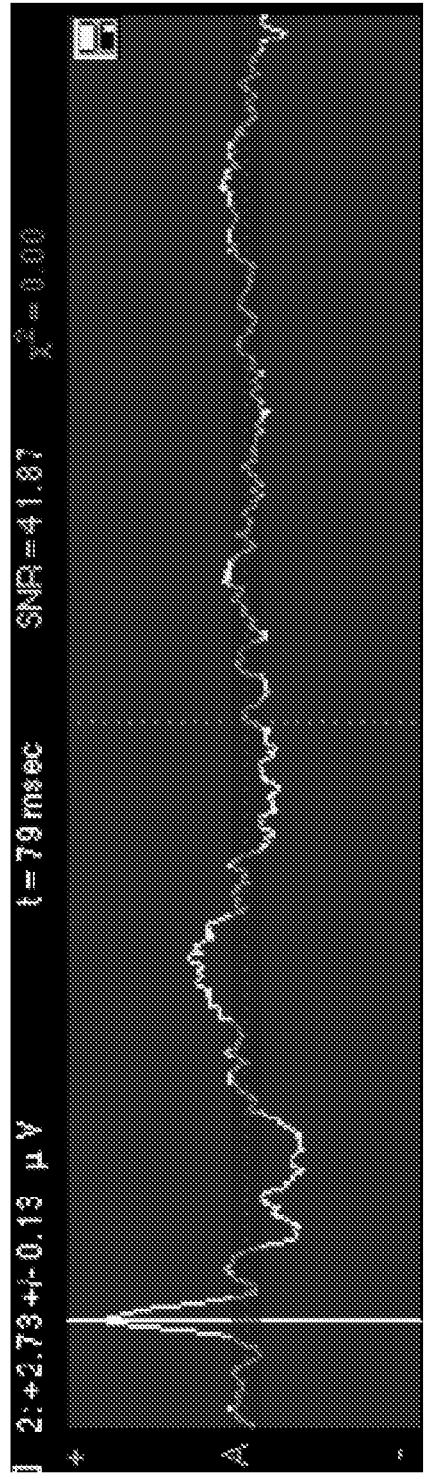

FIGS. 17A and 17B depict averaged epoch measurements for EEG and EFEG signals, respectively, in accordance with certain embodiments. In a typical measurement the data first could be filtered if it carries 60 Hz or of its harmonics. There could also be other sources of noise (machines, inductive coils, etc.). In testing of the methods and apparatuses, both channels provided clean data. This is an indication that the electrodes were making a good electrical contact with the scalp and the amplifier was reducing the common mode noise. But a real-time observation of the power spectrum when the electrodes are placed is a check for the conductivity and the noise levels.

Typically around 300 epochs may be measured, each lasting around a second. After recording, epochs showing unusual spikes or saturations can be masked (could be due to EM noise interference or blinking, grinding teeth). After averaging we found the noise levels to be around 0.14 μV and 0.13 μV for EEG and the disclosed methods and apparatuses, respectively. This shows the noise to be uncorrelated across each pair of electrodes due to the different separations between the pairs. So the noise could be electrode/amplifier origin. EFEG (the second trace) is quite different from EEG (the first trace) at longer latencies. Apparently, the later EEG peaks were produced by activations at the top of the head, where the EEG reference electrode was, or otherwise were very global, while EFEG shows only local (back of the head) activations. It is also possible that the later activations had potential gradient in vertical direction, which we didn't measure. But this is unlikely, usually; the potential varies more horizontally than vertically over the back of the head.

Figure 18A:
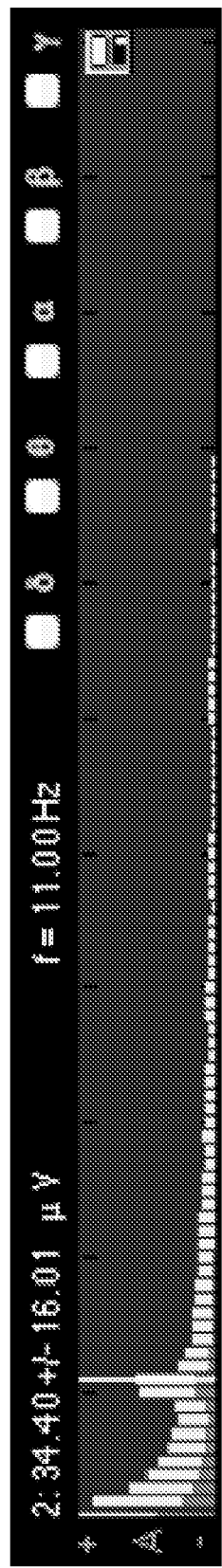
FIG. 18 illustrates further EEG and EFEG measurements, in accordance with some embodiments.
Figure 18B:
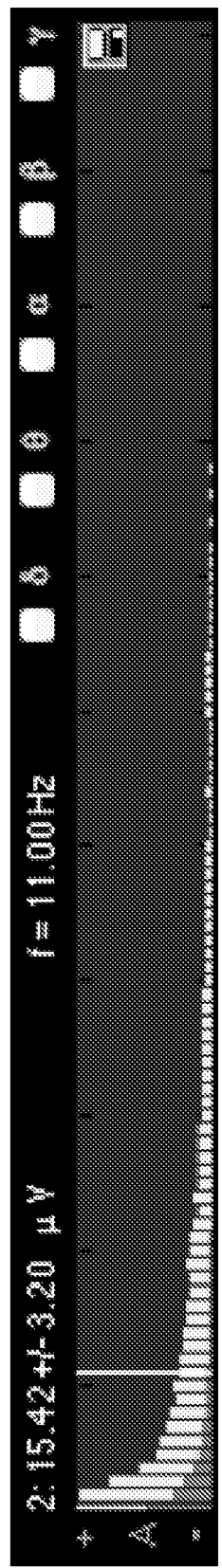

FIGS. 18A and 18B depicts a comparison of EEG and EFEG data, respectively, showing alpha (eyes closed) and beta (counting) signals for 120 seconds each, in accordance with certain embodiments. In FIG. 18B, a fast Fourier transform (FFT) shows significant Alpha and Beta activities on both channels—well defined humps can be seen around 10 and 20 Hz. So EFEG is capable of picking up alpha and beta waves as well as evoked responses. Alpha comes out quite clearly, although it is considerably weaker than in EEG, which is not surprising given alpha's global distribution. Beta is not visible, but this is also not surprising because on subject's head it is all in the front. Beta is much more focal than alpha, so it should be easy to see on a frontal EFEG electrode. In FIG. 18A, the corresponding EEG data has a fairly strong 60 Hz peak which is completely gone in FIG. 18B, showing EFEG. This demonstrates that a close reference electrode indeed cuts down on external noise.

Figure 19:
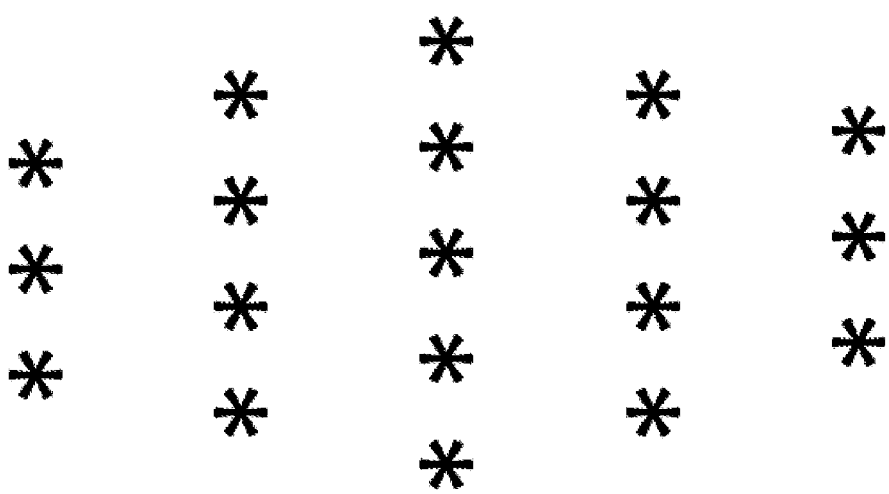
FIG. 19 illustrates a hexagonal array of sensors, in accordance with some embodiments.

FIG. 19 depicts a hexagonal array of 19 tri-polar sensors covering the back of the head, in accordance with certain embodiments. This can be done by using a conductive gel, or may be performed without it. Active electrodes may be used. All sensors may be held next to the scalp, and the 18 tri-polar sensors may be mounted on their own small platforms to a swimming cap and then bandaging over the cap, if it is necessary to make the contact tighter. More electrodes may be used in other embodiments. These could be a combination of bipolar electrodes, giving tri-polar or multipolar electrodes. These electrode networks could have one signal ground. This is where all the bipolar electrodes are connected and grounded at one location. This will depend on the noise level of the system.

The disclosed methods and apparatuses can be combined with other electric field measurement sensors. A non-contact sensor using a high impedance electrometer with feedback (Prance et al., 2008) may be used to observe alpha rhythms. An electro-optical sensor has demonstrated observation of EEG signals with dry electrodes in skin contact (Kingsley et al., 2004). Several other approaches to fiber optic sensors for electric fields have been demonstrated which could be used for EFEG (Gutierrez-Martinez et al., 2011; Runde et al., 2007; Gibson, 2009). None of these techniques have been utilized to measure directional properties of the electric field at the skull that are required for EFEG. These sensors appear to have sensitivity <1 mV per meter sufficient to measure electric fields of the brain, but 10 to 100× improvement in sensitivity may lead to observation of more brain signals and greatly improved source localization.

2. Calculating the Electric Field Produced by a Dipole Current Source

In some aspects, the methods and apparatuses disclosed herein calculate the electric field produced by a dipole current source positioned inside a set of concentric spherical shells with homogenous anisotropic conductivity inside each shell. Parameters of the spherical head model, BEM head model, and the simulation parameters that are used to estimate the number of uncorrelated brain signals and source localization error are explained.

By 2.1. Poisson Equation

The derivation follows de Munck (1988) with some corrections and modifications for calculating electric field outside of the spherical shells. We start with the current-conservation equation, which also defines the volume source current s(r, t):

$$\nabla \cdot J(r;t) \equiv s(r;t), \quad (1)$$

where r and t are positions in space and time respectively. Because for bioelectric brain signals the electric currents can be considered static (Nunez & Srinivasan, 2006, Appendix B), the time variable t may be suppressed for the rest of the discussion. Using Ohm's law J(r)=σ(r)E(r), and writing electric field E as negative gradient of the electric field potential Φ, the current conservation equation can be written as Poisson's equation for potentials:

$$\nabla \cdot J(\sigma(r)\nabla\Phi(r)) = -s(r). \quad (2)$$

Here σ stands for electrical conductivity tensor. In the following we assume that the conductivity tensor is diagonal, has two equal tangential components η(r), and a radial component ε(r), which depend on radius r only. This corresponds to a model consisting of an arbitrary number of concentric spherical shells with radial-tangential anisotropic conductivity. Taking divergence and gradient in spherical coordinates transforms (2) to $$\frac{1}{r^2}\frac{\partial}{\partial r}\left(r^2\varepsilon(r)\frac{\partial \Phi}{\partial r}\right) + \frac{\eta(r)}{r^2\sin\theta}\frac{\partial}{\partial \theta}\left(\sin\theta\frac{\partial \Phi}{\partial \theta}\right) + \frac{\eta(r)}{r^2\sin^2\theta}\frac{\partial^2 \Phi}{\partial \phi^2} = -s(r, \theta, \phi). \quad (3)$$

2.2. Monopole Potential

To calculate electric field of a dipole current source we first find solution of the above equation for a monopole source, i.e., its Green's function G(r, r0) for the source at r0=(r0, θ0, φ0) and observation point at r=(r,θ,φ). In this case the right-hand side of (3) is the Dirac delta function written in spherical coordinates. It is equal to 0 everywhere except r=r0 and it integrates to 1 over the whole space:

$$s(r, \theta, \phi) = \frac{1}{r^2 \sin\theta}\delta(r-r_0)\delta(\theta-\theta_0)\delta(\phi-\phi_0) \quad (4)$$

Green's function for Poisson's equation can be found by variable separation (e.g., Morse & Feshbach, 1953, Chs. 5, 7). To this end, G(r, r0) can be written as the following expansion in spherical harmonics Y m l(θ, φ), which are eigen functions of the angular part of (3) with eigenvalues—l(l+1)

$$G(r, r_0) = \sum_{l=0}^{\infty} R_l(r, r_0) \sum_{m=-l}^{m=l} \overline{Y}_l^m(\theta_0, \phi_0)Y_l^m(\theta, \phi) \quad (5)$$

where $$Y_l^m(\theta, \phi) = \sqrt{\frac{2l+1}{4\pi}\frac{(l-m)!}{(l+m)!}} P_l^m(\cos\theta)e^{im\phi} \quad (6)$$

are normalized spherical harmonics, and Pml(x) stand for the associated Legendre polynomials. Although spherical harmonics are complex functions, and Yml stands for complex conjugation of Y ml, G(r, r0) is real, because the summation of—m and m terms combines two complex exponents into a real cosine function. Keeping spherical harmonics in complex form simplifies the following derivation.

Multiplying (3) by r2, then substituting (4) as the right-hand part and (5) in place of Φ gives $$\sum_{l=0}^{\infty} \sum_{m=-l}^{m=l} \overline{Y}_l^m(\theta_0, \phi_0)Y_l^m(\theta, \phi) \quad (7)$$
$$\left(\frac{\partial}{\partial r}\left(r^2\varepsilon(r)\frac{\partial R_l(r, r_0)}{\partial r}\right) - l(l+1)\eta(r)R_l(r, r_0)\right) =$$
$$-\frac{\delta(r-r_0)\delta(\theta-\theta_0)\delta(\phi-\phi_0)}{\sin\theta}.$$

Due to orthonormality of spherical harmonics, multiplying the above equation by Ym'l'(θ, φ) and integrating over angles results in a set of ordinary differential equations:

$$\frac{\partial}{\partial r}\left(r^2\varepsilon(r)\frac{\partial R_l(r, r_0)}{\partial r}\right) - l(l+1)\eta(r)R_l(r, r_0) = -\delta(r-r_0) \quad (8)$$

This is a case of the well-known Sturm-Liouville equation. Its solution (Green's function) can be constructed from two independent solutions R1 and R2 of the homogeneous equation (e.g., Morse & Feshbach, 1953, Ch. 7). The solutions are easily found, when the model conductivities ε(r) and η(r) are piece-wise constant, i.e., constant within each spherical shell. Then, $$R_{1,2}(r) = A^{1,2}r^\lambda + \frac{B^{1,2}}{r^{\lambda+1}} \quad (9)$$

satisfy the homogeneous form of equation (8) for any A and B, if $$\lambda = \sqrt{l(l+1)\frac{\eta}{\varepsilon} + \frac{1}{4}} - \frac{1}{2}. \quad (10)$$

λ=1 for isotropic shells (η=ε), otherwise it depends on the anisotropy ratio η/ε and therefore differs among shells. A and B coefficients are calculated for each shell to satisfy its boundary conditions.

We seek Green's function of the Sturm-Liouville equation (8) as R1 to the left of the monopole position r0, and as R2 to the right of it:

$$R(r, r_0) = \begin{cases} aR_1(r); & 0 < r \leq r_0 \\ bR_2(r); & r_0 \leq r < \infty \end{cases} \quad (11)$$

There are two unknown scaling factors, a and b. Continuity of the solution at r0 gives the first constraint, $$aR_1 = bR_2 \quad (12)$$

Integrating (8) from r0−δ to r0+δ for infinitesimal δ gives the second constraint at r0, $$\epsilon r^2(bR'_2 - aR'_1) = -1 \quad (12)$$

Solving the last two equations for a and b gives $$R(r, r_0) = c \begin{cases} R_1(r)R_2(r_0); & 0 < r \leq r_0 \\ R_1(r_0)R_2(r); & r_0 \leq r < \infty \end{cases} \quad (14)$$

where $$\frac{1}{c} = -\epsilon r^2(R_1 R'_2 - R'_1 R_2) = \epsilon(2\lambda - 1)(A^1 B^2 - A^2 B^1). \quad (15)$$

is the normalization constant calculated at r0. Note, that although c formally depends on the source position r0 it is a constant and does not vary with r0. It is always possible to choose r≤r0 inside the innermost shell, therefore, to avoid divergence at r=0 we require B1=0 there. Because the solution is eventually normalized by c, one is free to set A1=1 in this shell, which makes it convenient to calculate c as follows:

$$c = \frac{1}{\epsilon_1(2\lambda_1 - 1)B_1^2}, \quad (16)$$

where the subscript indicates the shell index (1 for the innermost shell).

The remaining A1j and B1j coefficients are calculated in a recurrent fashion starting from A11 and B11 so as to satisfy boundary conditions across shell boundaries rj. The two conditions are the continuity of potential, $$\left(A^1 r^\lambda + \frac{B^1}{r^{\lambda+1}}\right)\bigg|_j^{j+1} = 0 \quad (17)$$

and the continuity of normal current. The current is given by Ohm's law applied to the radial component of the electric field, $$\epsilon\left(A^1 \lambda r^{\lambda-1} - \frac{B^1(\lambda+1)}{r^{\lambda+2}}\right)\bigg|_j^{j+1} = 0 \quad (18)$$

Here j and j+1 indices numerate shells that share boundary j. These subscripts are common for all A, B, λ, ε, and r symbols in the above two formulas.

Coefficients A2j and B2j are calculated in the same fashion, but starting from the outermost shell N, which extends to infinity, and then moving inward. Because for the outermost shell one can always choose r0≤r, it follows that A2N=0 to avoid divergence at infinity. Again, due to eventual normalization by c, one is free to set B to any number in this shell, so we set B2 N=1.

Finally, substituting (14) in (5) gives the monopole potential for our model. Because we are mostly interested in the case where observation points are outward of the sources, we obtain for r0≤r:

$$\Phi_{mon}(r, r_0) = \sum_{l=0}^{\infty} c_l R_l^1(r_0) R_l^2(r) \sum_{m=-l}^{m=l} \overline{Y}_l^m(\theta_0, \phi_0) Y_l^m(\theta, \phi) \quad (19)$$

The solution is real and invariant with respect to swapping source and observation points (R superscripts have to be swapped as well), which reflects Lorentz reciprocity.

2.3. Dipole Potential

The dipole potential is obtained from the monopole solution as follows:

$$\Phi_{dip}(r, r_0) = I\Phi_{mon}(r, r_0 + \delta/2) - I\Phi_{mon}(r, r_0 - \delta/2) \quad (20)$$
$$= I\delta \cdot \nabla_{r_0} \Phi_{mon}(r, r_0),$$

where I is the magnitude of the source and sink currents, and δ is an infinitesimal vector pointing from negative (sink) to positive source. Taking the limit of |δ|→0 and setting I=q/|δ| defines the dipole moment q as $$q = q\hat{\delta} \quad (21)$$

and $$\Phi_{dip}(r, r_0) = q \cdot \nabla_{r_0} \Phi_{mon}(r, r_0). \quad (22)$$

Prior to taking the gradient some simplifications are necessary to keep the math tractable. Without a loss of generality we can assume that the dipole location r0 is at r0 along the z-axis. The dipole azimuth φ0 is defined by the azimuth of the dipole moment d in this case. Then, the ˆφ component of the gradient taken in spherical coordinates is orthogonal to d, and the corresponding term q·●φ0 vanishes. Given that θ0=0 and, therefore, Y ml (θ0, φ0) is non-zero only if m=0, the r and θ components of the gradient are given by the following formulas:

$$\nabla_{r_0} \Phi_{mon}(r, r_0) = \sum_{l=0}^{\infty} c_l \frac{dR_l^1(r_0)}{dr_0} R_l^2(r) \frac{2l+1}{4\pi} P_l^0(\cos\theta) \quad (23)$$

$$\nabla_{\theta_0} \Phi_{mon}(r, r_0) = -\frac{1}{r_0} \sum_{l=0}^{\infty} c_l R_l^1(r_0) R_l^2(r) \frac{2l+1}{4\pi} P_l^1(\cos\theta)\cos(\phi - \phi_0) \quad (24)$$

To obtain the latter formula we used the following identity for the associated Legendre polynomials:

$$2\frac{dP_l^m(\cos\theta)}{d\theta} = P_l^{m+1}(\cos\theta) - (l+m)(l-m+1)P_l^{m-1}(\cos\theta) \quad (25)$$

Therefore, $$\frac{dP_l^m(\theta_0)}{d\theta_0} \neq 0 \quad (26)$$

only if $m = \pm 1$ and

-continued $$\sum_{m=-l}^{m=l} \frac{\partial \overline{Y}_l^m(\theta_0, \phi_0)}{\partial \theta_0} Y_l^m(\theta, \phi) = \frac{2l+1}{4\pi} \quad (27)$$

$$\left( \frac{(l+1)!}{(l-1)!} P_l^{-1}(\cos\theta) \frac{e^{-i(\phi-\phi_0)}}{2} - (l+1)l \frac{(l-1)!}{(l+1)!} P_l^1(\cos\theta) \frac{e^{i(\phi-\phi_0)}}{2} \right) =$$

$$-\frac{2l+1}{4\pi} P_l^1(\cos\theta)\cos(\phi - \phi_0)$$

where another identity, $$P_l^{-m}(x) = (-1)^m \frac{(l-1)!}{(l+1)!} P_l^m(x), \quad (28)$$

may be used.

Substituting (9), (16), (23), and (24) in (22) solving the Poisson's equation for the spherical shells model we obtain for the dipole potential:

$$\Phi_{dip}(r, r_0) = \frac{1}{4\pi\epsilon_1 B_1^2} \quad (29)$$

$$\sum_{l=1}^{\infty} \frac{2l+1}{2\lambda_1+1} \left( A^2 r^\lambda + \frac{B^2}{r^{\lambda+1}} \right)_j \times \left[ q_r \left( \lambda A^1 r_0^{\lambda-1} - (\lambda+1) \frac{B^1}{r_0^{\lambda+2}} \right)_{j0} \right.$$

$$\left. P_l^0(\cos\theta) - q_\theta \left( A^1 r_0^{\lambda-1} + \frac{B^1}{r_0^{\lambda+2}} \right)_{j0} P_l^1(\cos\theta)\cos(\phi - \phi_0) \right]$$

where the j0 and j subscripts stand for source and observation point shell indices respectively. These subscripts are common for all A, B, and λ symbols inside their respective parentheses. qr=q cos α and qθ=q sin α stand for radial and tangential dipole components respectively; a is the angle between the dipole moment q and z-axis. It is worth noting that the analogous formula derived by de Munck (1988) (equation 35) has incorrect overall sign as well as incorrect relative sign between qr and qθ. These errors resulted from several sign confusions in the course of derivation by de Munck. It may also be derived assuming isotropic innermost shell, in which case the 2l+1/2λ1+1 factor in (29) is 1.

2.4. Dipole Electric Field

Electric field of a current dipole is calculated by taking negative gradient of (29) with respect to r. For the radial component, $$E_r(r, r_0) = -\frac{1}{4\pi\epsilon_1 B_1^2} \sum_{l=1}^{\infty} \frac{2l+1}{2\lambda_1+1} \left( \lambda A^2 r^{\lambda-1} - (\lambda+1)\frac{B^2}{r^{\lambda+2}} \right)_j \times \quad (30)$$

$$\left[ q_r \left( \lambda A^1 r_0^{\lambda-1} - (\lambda+1)\frac{B^1}{r_0^{\lambda+2}} \right)_{j0} P_l^0(\cos\theta) - \right.$$

$$\left. q_\theta \left( A^1 r_0^{\lambda-1} + \frac{B^1}{r_0^{\lambda+2}} \right)_{j0} P_l^1(\cos\theta)\cos(\phi - \phi_0) \right].$$

For the inclination (θ) component, using (25), $$E_\theta(r, r_0) = -\frac{1}{4\pi\epsilon_1 B_1^2} \sum_{l=2}^{\infty} \frac{2l+1}{2\lambda_1+1} \left( A^2 r^{\lambda-1} + \frac{B^2}{r^{\lambda+2}} \right)_j \times \quad (31)$$

$$\left[ q_r \left( \lambda A^1 r_0^{\lambda-1} - (\lambda+1)\frac{B^1}{r_0^{\lambda+2}} \right)_{j0} P_l^0(\cos\theta) - q_\theta \left( A^1 r_0^{\lambda-1} + \frac{B^1}{r_0^{\lambda+2}} \right)_{j0} \right.$$

$$\left. \frac{1}{2}[P_l^2(\cos\theta) - l(l+1)P_l^0(\cos\theta)]\cos(\phi - \phi_0) \right].$$

For the azimuth (φ) component, $$E_\phi(r, r_0) = -\frac{1}{4\pi\epsilon_1 B_1^2} \sum_{l=2}^{\infty} \frac{2l+1}{2\lambda_1+1} \left( A^2 r^{\lambda-1} + \frac{B^2}{r^{\lambda+2}} \right)_j \times \quad (32)$$

$$q_\theta \left( A^1 r_0^{\lambda-1} + \frac{B^1}{r_0^{\lambda+2}} \right)_{j0} \frac{P_l^1(\cos\theta)}{\sin\theta} \sin(\phi - \phi_0).$$

Note that the division by sin θ in the above formula does not result in divergence for θ=0, because P11(θ)~sin θ for |θ|→0.

2.5. Checking the Solution

Results (29), (30), (31), (32) may be validated numerically in two ways. First, the radial part of the solution (due to qr) can be checked against the tangential part (due to qθ) by positioning the dipole in the center of the spherical model (r0=0). The two solutions should be identical up to π=2 rotation. To this end, a unit current dipole may be positioned in the center of a 4-shell model (see Section 2.6 for details). The dipole may be oriented along the z-axis in one case and along the y-axis in the other case. The corresponding solutions may be found identical up to the π=2 rotation bringing z-axis to y-axis.

$$\Phi_{dip}(r, r_0) = \frac{q_r}{4\pi\epsilon} \left( 2\frac{r\cos\theta - r_0}{d^3} + \frac{\frac{1}{d} - \frac{1}{r}}{r_0} \right) + \quad (33)$$

$$\frac{q_\theta}{4\pi\epsilon} \left( 2\frac{r}{d^3} + \frac{\frac{1}{d} + \frac{1}{r}}{r - r_0\cos\theta + d} \right) \sin\theta\cos(\phi - \phi_0),$$

where r is the sphere's radius, and d=|r−r0| (Zhang, 1995). The corresponding electric field formulas are given in the Appendix. A comparison to the single-sphere solution may be made by calculating solution for a 4-shell model (see Results for details) with conductivities η=ϵ=1 for all 4 shells. Several dipole orientations and positions were tested. The results were identical to those given by (33) and the associated electric field formulas (A2) given below.

The electric field for a 1-sphere model is given as follows. Surface dipole potential for a 1-sphere isotropic and homogeneous model is given by (33). Introducing the following shorthand notation, $$d = r - r_0 \quad (A.1)$$

$$s = \frac{1}{d} + \frac{1}{r}$$

$$t = \frac{1}{d} - \frac{1}{r}$$

-continued $$a = r - r_0\cos\theta$$
$$b = r\cos\theta - r_0$$
$$c = \frac{2r}{d^3} + \frac{s}{a+d},$$

and taking negative gradient in spherical coordinates gives the following expressions for the electric field on the surface of the sphere, $$E_r = \frac{q_r}{4\pi\epsilon}\left(\frac{6ab}{d^5} - \frac{2\cos\theta}{d^3} + \frac{a}{r_0 d^3} - \frac{1}{r_0 r^2}\right) + \quad (A.2)$$

$$\frac{q_\theta}{4\pi\epsilon}\left(\frac{6ra}{d^5} - \frac{2}{d^3} + \frac{\frac{a}{d^3} + \frac{1}{r^2} + \frac{l}{d}}{a+d}\right)\sin\theta\cos(\phi - \phi_0)$$

$$E_\theta = \frac{q_r}{4\pi\epsilon}\left(\frac{6r_0 b\sin\theta}{d^5} + \frac{3\sin\theta}{d^3}\right) +$$

$$\frac{q_\theta}{4\pi\epsilon}\left(r_0\left(\frac{6r}{d^5} + \frac{\frac{a+d}{d^3} + s^2}{(a+d)^2}\right)\sin^2\theta - \frac{c}{r}\cos\theta\right)\cos(\phi - \phi_0)$$

$$E_\phi = \frac{q_\theta}{4\pi\epsilon}\frac{c}{r}\sin(\phi - \phi_0)$$

2.6. Spherical Head Model Parameters

Figure 20:
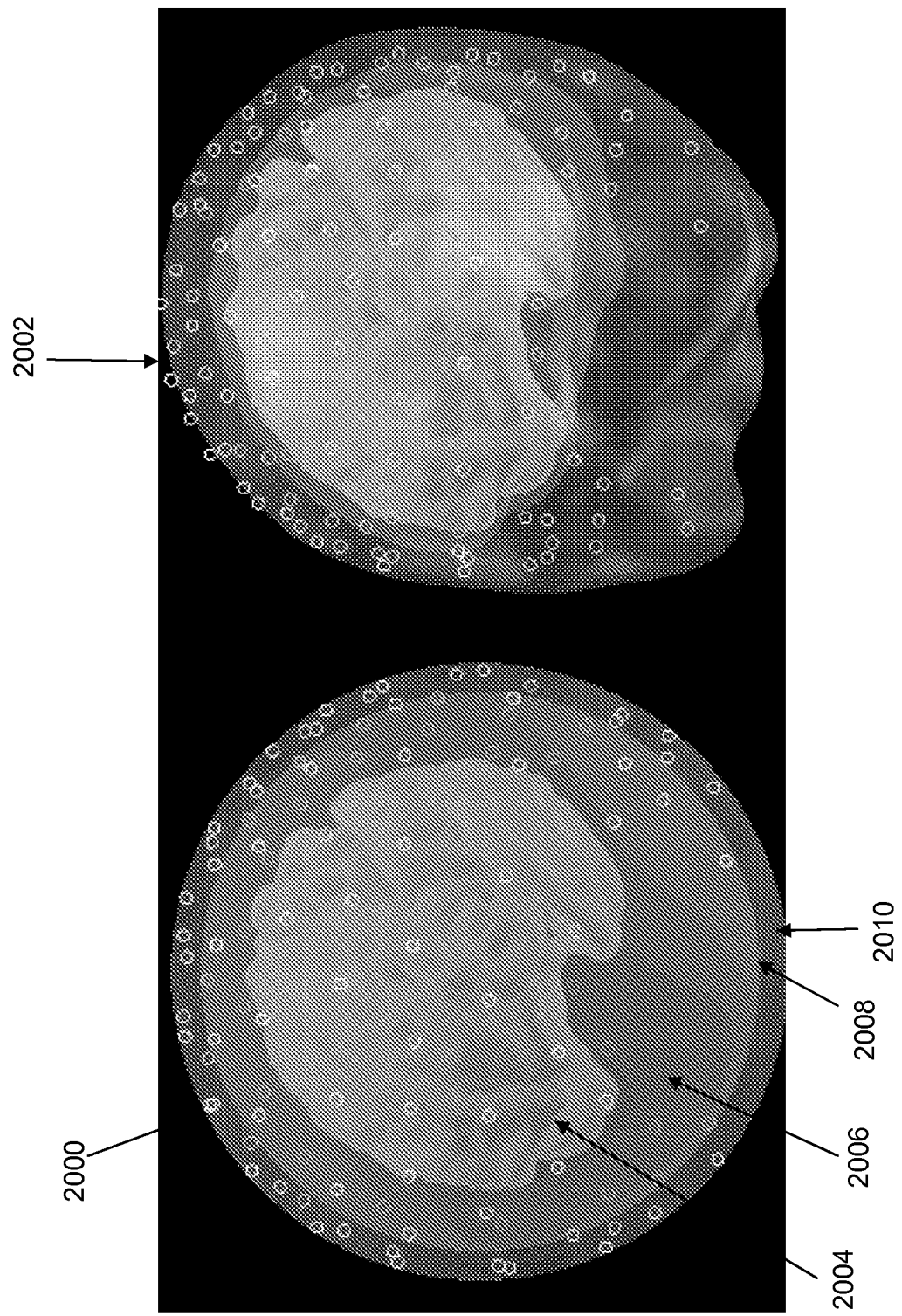
FIG. 20 illustrates spherical and boundary element head models, in accordance with some embodiments.

FIG. 20 illustrates spherical and boundary element head models in accordance with certain embodiments. Spherical head model 2000 and boundary element (BEM) head model 2002 are shown. A 4-shell spherical model may be used for simulations. The shells are (from innermost to outermost): brain (white and gray matter) 2004, cerebro-spinal fluid (CSF) 2006, skull (tables and diploe layers) 2008, and scalp (muscle, fat, and skin) 2010. Spherical model parameters typical for human head tissue simulation may be used. The radii of the brain, SCF (cerebro-spinal fluid), inner skull, outer skull, and scalp spheres were 9, 9.1, 9.2, 9.7, and 10.2 cm respectively (FIG. 20). The brain shell radius (9 cm) may be chosen to fit the averaged pial surface used in simulations for placing current dipoles (FreeSurfer averaged brain, see Section 2.8). The shells radial conductivities were set to 0.3, 1.5, 0.006, and 0.3 S/m for brain, SCF, skull, and scalp respectively. Tangential conductivities were equal to radial conductivities (isotropic conductivity) except for the skull shell, where the tangential conductivity may be set to 0.06, i.e., a 10-fold anisotropy may be assumed due to the higher conductivity of the diploe layer compared to the table layers of the skull. The values were based on the available anatomical data (discussed in Nunez & Srinivasan, 2006, chs. 4 and 6) and also in Haueisen et al. (2002); Hoekema et al. (2003); Wolters et al. (2006); Güllmar et al. (2010). Other conductivity ratios were tried as well (isotropic skull, 5× more conductive skull), but these manipulations did not change the results in an important way.

2.7. BEM Head Model

A boundary element (BEM) head model may be constructed based on high-resolution MRI data averaged over 40 subjects; the data is distributed as a part of the FreeSurfer toolbox (Dale et al., 1999). The BEM head-model include the three volumes shown in FIG. 1: scalp, skull, and CSF/brain; the volumes were reconstructed from the group-averaged MRI data with the help of the FSL toolbox (Woolrich et al., 2009). The BEM solution to Equation (2) may be calculated numerically using MNE Suite toolbox (Hämäläinen & Sarvas, 1989). The tangential components of the electric field Eθ and Eφ were obtained from the potential by numeric differentiation: the potential may be calculated at triplets of points on the scalp, the first point in a triplet may be at the location of a given sensor, the other two were displaced from the electrode location by 1 mm in the azimuthal and inclinational directions respectively (FIG. 5, left panel). The radial component of the electric field need not be calculated. To improve the BEM precision the inner skull may be meshed as the 5-th subdivision of icosahedron (20,480 triangles), the outer skull and scalp surfaces were meshed as the 4-th subdivision of icosahedron (5,120 triangles). Conductivities of the three volumes were set to 0.3, 0.006, and 0.3 S/m for scalp, skull and CSF/brain respectively. Because BEM method can only be applied to isotropic volumes skull anisotropy need not be modeled.

2.8. Cortical Sources

Cortical surface of the group-averaged data provided with the FreeSurfer toolbox may be used to place current dipoles in simulations. 10,242 current dipoles were positioned at the nodes of a triangular mesh (5-th subdivision of icosahedron, mid-gray FreeSurfer mesh) for left and right cortex. The neurologist's "rule of thumb" is that at least 6 cm2 of cortex has to be active to record scalp potentials without averaging (e.g., Nunez & Srinivasan, 2006, ch. 1.8 and references therein). Correspondingly, a simulated source patch included a single dipole and all its nearest neighbors up to the third-degree, which gave 37 dipoles altogether: 1+6+12+18=37. The patches were, therefore, roughly hexagonal in shape approximately 2.5 cm in diameter when measured along the cortical surface. This corresponded to 5 cm2 of cortical area, close to the "rule of thumb" size. The source patch may be positioned at the nodes of a uniform grid (4th subdivision of icosahedron, 2,562 nodes) covering each hemisphere to simulate various cortical activation sites.

The dipole orientations were fixed to be orthogonal to the cortical surface, which reflects the common assumption that EEG and MEG are due to synaptic currents produced by activity of cortical piramidal cells. These currents flow along the cells axons primarily perpendicular to the cortex. The magnitude of the source dipoles may be equal among the 37 dipoles constituting a source patch and may be such as to produce the maximum scalp potentials (for the most superficial sources) about 10 μV, which is typical for evoked potentials (e.g., P100 or P300).

2.9. Sensors

Realistic sensor locations were used by averaging a 128-channel HydroCell GSN net (EGI Inc.) electrode location applied to 34 subjects. The electrode locations were measured for each subject using a Polhemus FASTRACK digitizer. The locations were projected onto the spherical scalp for the spherical head model and slightly stretched and shifted by an affine transformation to better fit the scalp for the BEM head model.

The resulting sensor locations are shown in FIG. 1, which illustrates spherical and BEM head models, in accordance with certain embodiments. Scalp, skull, CSF, and brain shells are shown in various colors. The BEM model makes no distinction between SCF and brain shells, both are shown in green. Pial cortical surface is shown in pink. Yellow circles mark sensor locations based on 128-channel Hydro-Cell GSN electrode net (EGI Inc.).

3. Analyzing Electric Fields

Electric fields produced by a single current dipole positioned inside the brain shell of the spherical model may be analyzed and used to provide localization. The number of uncorrelated signals offered by electric fields (EFEG) and their potentials (EEG) may be evaluated by the principal component analysis (PCA) for spherical and BEM head models. Finally, the quality of source localization is compared between the EEG and EFEG methods using the BEM head model.

3.1. Single Dipole Electric Fields

Figure 21:
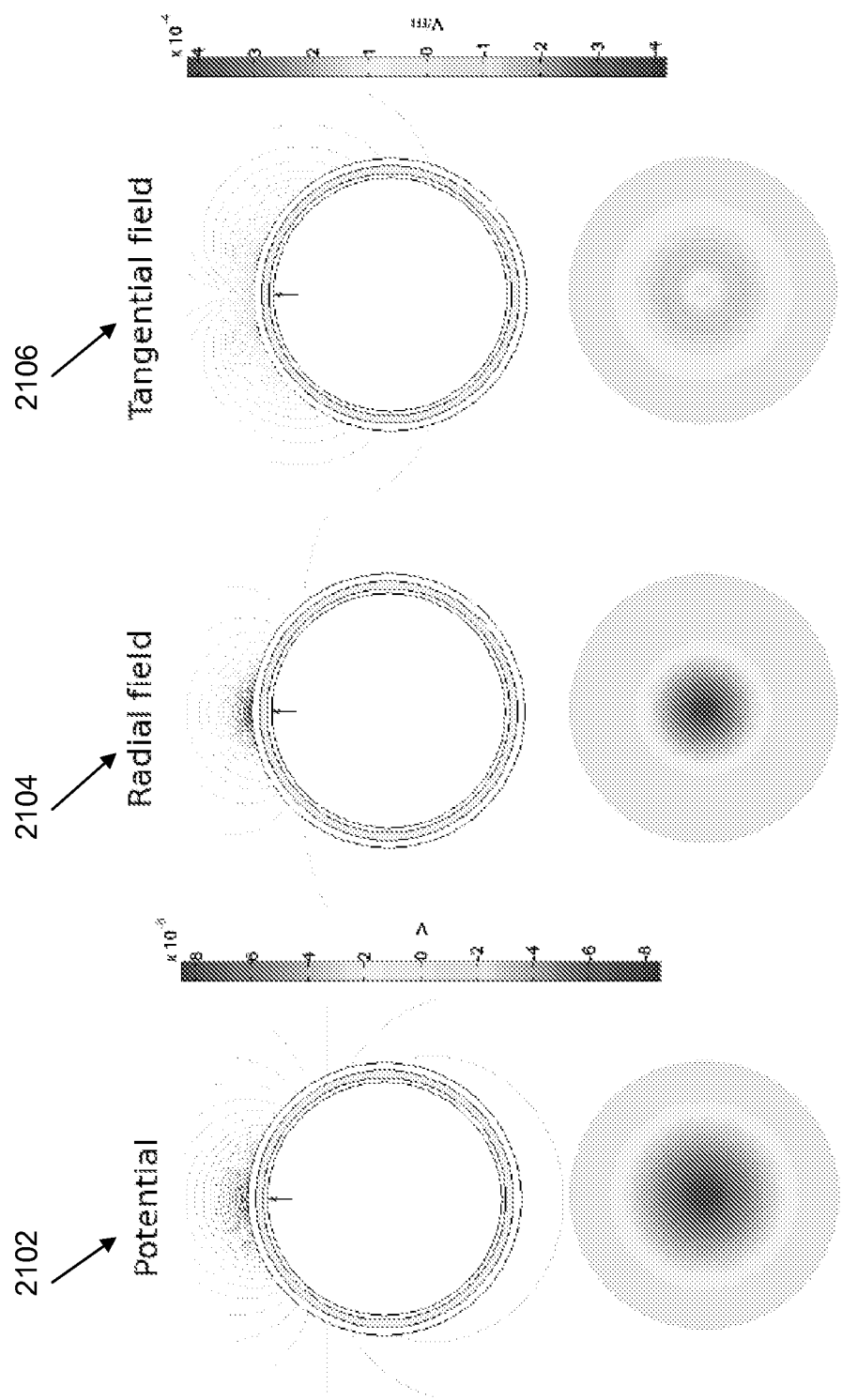
FIG. 21 illustrates a spherical head model, in accordance with some embodiments.

FIG. 21 illustrates a spherical head model, a radial current dipole, in accordance with certain embodiments. Equations (29-32) were used to calculate electric potential 2102 and field 2104, 2106 produced by a radial dipole (i.e., aligned perpendicular to the skull) positioned 1 cm below the skull surface. Potential and electric field magnitudes are shown by contour plots and color maps as indicated by the color bars. The color maps show signals on the spherical scalp surface. For the radial field 2104, 'cold' and 'hot' hues indicate inward and outward field directions respectively. For the tangential electric field 2106, only the 'hot' portion of the color map is used to indicate the field magnitudes. The potential is shown in the left panel, the radial electric field Er in the middle panel. The two tangential components $E\theta$ and $E\varphi$ are represented by the tangential field magnitude given by $Et=\sqrt{E^2\theta+E^2\varphi}$ shown in the right panel. Electric potential and field fall off approximately as the square and cube of the distance from the dipole respectively. The radial field component has a discontinuity at the scalp surface, its value just below the surface is zero because there is no current flowing radially at the head boundary. The tangential field component extends continuously from the head volume into the air.

Dipolar electric field on or near the head surface is approximately $4\times10^{-4}$ V/m at its maximum versus a $8\times10^{-6}$ V maximum for electric potential, which is the range of typical values for EEG evoked potentials). The radial field is about 3 times stronger than the tangential field at their maxima. Unlike the radial component, which similarly to the potential forms a 'hotspot' on the scalp above the dipole location, the tangential component has a ring-shaped distribution centered over the dipole. The radial and tangential field patterns are more focused than the potential pattern.

Figure 22:
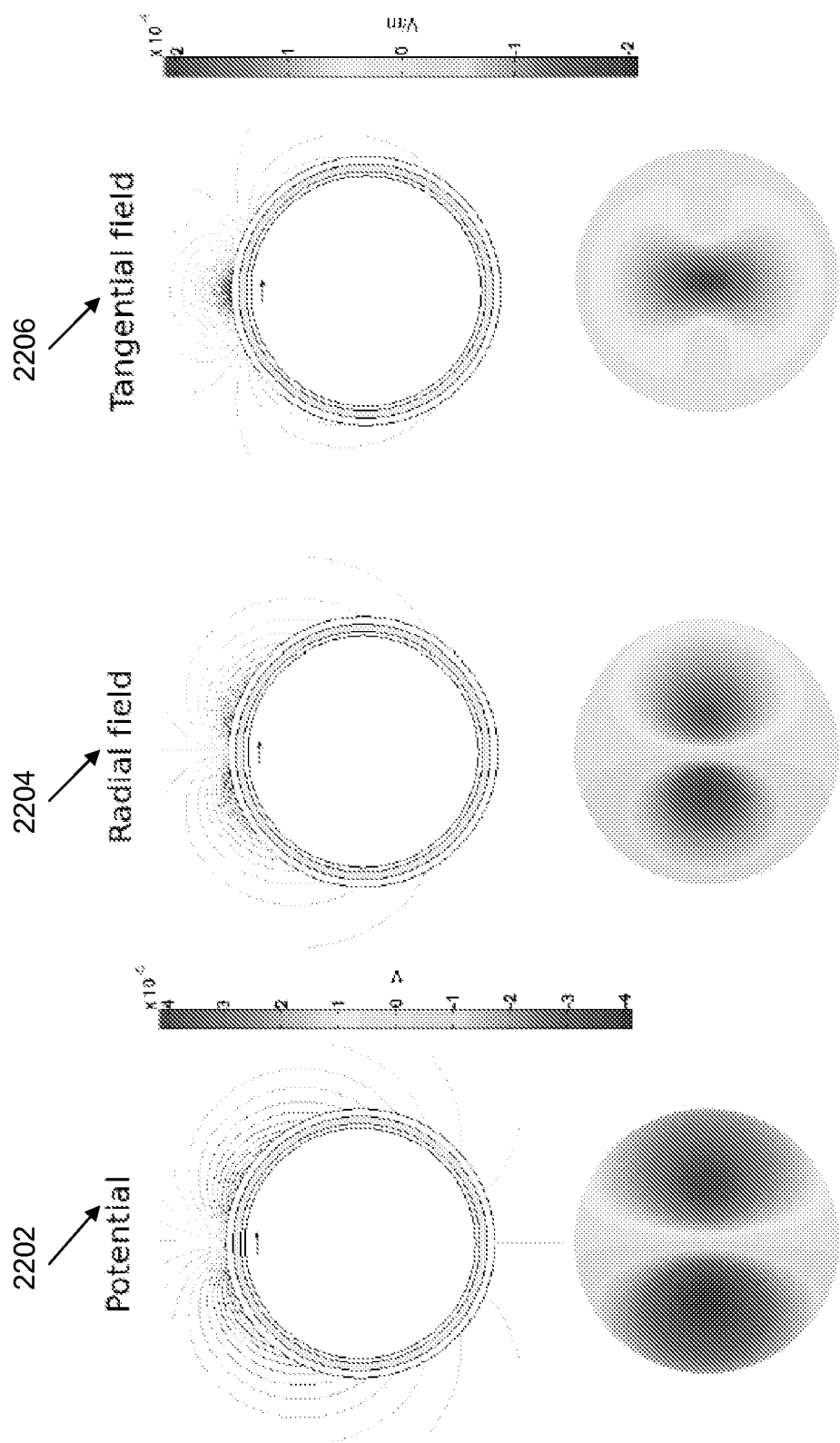
FIG. 22 illustrates another spherical head model, in accordance with some embodiments.

FIG. 22 illustrates another spherical head model, a tangential current dipole, in accordance with certain embodiments. Potential 2202 and electric field magnitudes 2204, 2206 are shown by contour plots and color maps as indicated by the color bars. The color maps show signals on the spherical scalp surface. For the radial field 2204, 'cold' and 'hot' hues indicate inward and outward field directions respectively. For the tangential electric field 2206, only the 'hot' portion of the color map is used to indicate the field magnitudes. Electric potential and field produced by a tangential dipole (i.e., aligned tangentially to the skull) positioned 1 cm below the skull surface are shown. The same as for the radial dipole, the scalp distribution of the radial component of the electric field is similar to the distribution of the potential, forming the typical 'dipolar' pattern. The tangential field magnitude is distributed in a different, 'dumbbell' pattern, the dumbbell being positioned above the dipole with its axis oriented perpendicular to the dipole axis. The maximal radial and tangential electric field magnitudes are about the same and close to the maximal tangential field for the radial dipole. The same as for the radial dipole, the field pattern on the scalp is more focused than the potential pattern.

FIG. 22 illustrates a boundary-element (BEM) head model in accordance with certain embodiments. Unlike the spherical head model the BEM model has a realistic head shape and variable thickness of the shells across the head surface. Electric field sensor locations on the scalp and their orientations (red for inclination, cyan for azimuth) are shown in the left panel 2202. Magnitude of the tangential component of the electric field on the scalp surface produced by (nearly) radial and tangential cortical sources are shown in the middle panel 2204 and right panel 2206. The left panel illustrates positions of the electric field sensors on the scalp, the red arrows indicating sensors measuring inclinational component $E\theta$, and the green arrows indicating sensors measuring the azimuthal component $E\varphi$. The tangential field magnitude Et is plotted in the next two panels using a colormap similar to the one used by the FreeSurfer and MNE Suite toolboxes. The middle panel shows Et for one of the simulated 5124 source patches (see Section 2.8) with dipoles oriented primarily in the radial direction. The right panel shows Et for a different source patch with dipoles oriented primarily in the tangential direction. Overall, Et field patterns obtained for the BEM head model are similar to the patterns produced by single dipoles for the spherical head model (FIGS. 12 and 13).

3.2. Number of Uncorrelated Signals

Given that electric field patterns shown in FIGS. 21 and 22 are more focused than potential patterns, and that there are 3 times more electric field measurements than potential measurements (if all 3 field components are measured), one might expect that electric field offers more information about brain sources than electric potential. The number of uncorrelated signals present in data is one possible metric of the information. This metric can be calculated by simulating many different cortical sources and evaluating how correlated the resulting sensor signals are. We simulated 5,124 source patches distributed evenly over the surface of left and right cortices (see Section 2.8 for details). The resulting potentials and electric fields were sampled by potential and field sensors positioned as shown in FIG. 1 and described in Section 2.9. Electric field components Er, $E\theta$, and $E\varphi$ at each sensor location were calculated for each source patch. Only tangential field components $E\theta$ and $E\varphi$ measured at the scalp surface were simulated for the BEM head model.

To determine the number of uncorrelated signals the principal component analysis (PCA) may be performed. First, a covariance matrix Cij for the sampled data mki may be calculated, the subscript indexing sensors (128 for the potential, 384 for the field) and the superscript indexing observations:

$$C_{ij}=\langle(m_i-\langle m_i\rangle)(m_j-\langle m_j\rangle)\rangle, \quad (34)$$

where the angular brackets denote averaging over N=5, 124 observations (the corresponding superscripts were omitted), each observation corresponding to a given simulated source patch. Then, the eigenvalues of the covariance matrix were calculated. The eigenvalues normalized by the largest eigenvalue for each set are plotted in FIG. 15 in the descending order. The PCA results for the scalp potential are plotted in red, the PCA results for electric field measured on the scalp are plotted in black, for the electric field measured 1 mm, 10 mm, and 30 mm away from the scalp in blue, cyan, and green respectively. Results for BEM head model are shown by thin curves.

Figure 23:
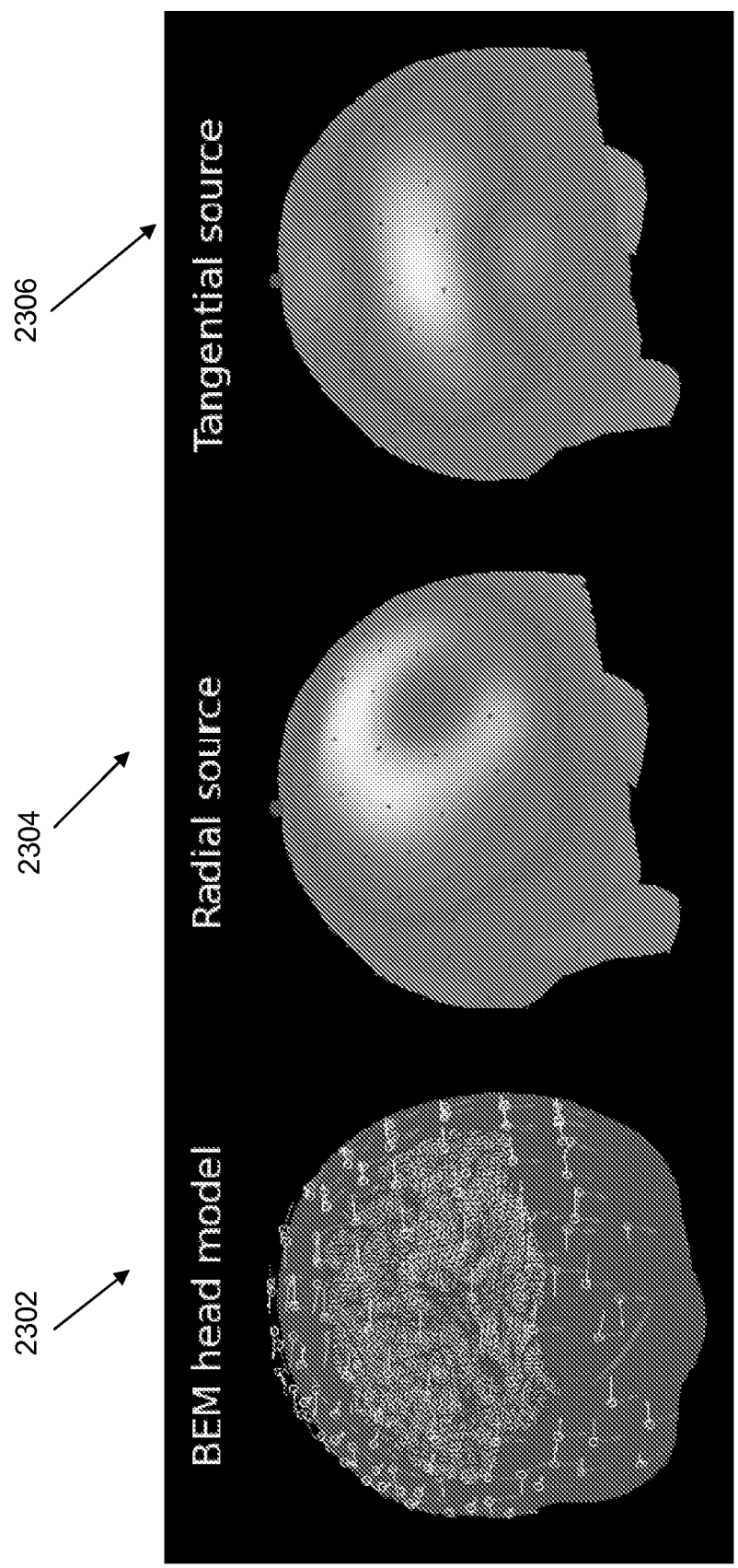
FIG. 23 illustrates a boundary element head model, in accordance with some embodiments.

The number of eigenvalues (x-axis) above a given noise-to-signal power (y-axis) determines the number of uncorrelated usable signals present in the data. One can see that electric field measurements appear to provide more usable signals than potential measurements for any noise level. As shown in FIG. 23, this is indicated by the electric field curves lying above the potential (red) curves with the exception of the green curve corresponding to EFEG sensors positioned 30 mm off the scalp.

To better see the increase in the number of usable signals between potential and field measurement the ratio of the two numbers for various noise-to-signal levels may be plotted in the inset. For the realistic range of noise-to-signal power (10-4-10-2) there were 2-3 times more usable signals in the field measurements than in the potential measurements, when the field may be measured on the scalp or 1 mm above it. For larger distances above the head the advantage may be quickly lost, so that at 30 mm the number of potential and field signals were about equal.

The increase in the number of uncorrelated signals did not occur just because there were 3 times more field sensors than potential sensors. To show this we simulated a 4-fold increase of the number of potential sensors by refining the 128-sensor mesh used for the rest of the simulations to 485-sensor mesh covering the same area of the head. The corresponding PCA results are plotted by the dashed orange curve. No significant increase in the number of usable signals except for unrealistically low noise levels (noise-to-signal power <10-6) resulted. As discussed in the Introduction, this was expected given the amount of low-pass filtering introduced by the skull.

The observed increase in the number of usable signals agrees with higher spatial resolution of bipolar EEG electrodes compared to conventional EEG electrodes (Srinivasan et al., 1996; Nunez et al., 1997). Provided that electrodes in a bipolar pair are sufficiently close-by their measurement approximates a tangential component of electric field.

Figure 24:
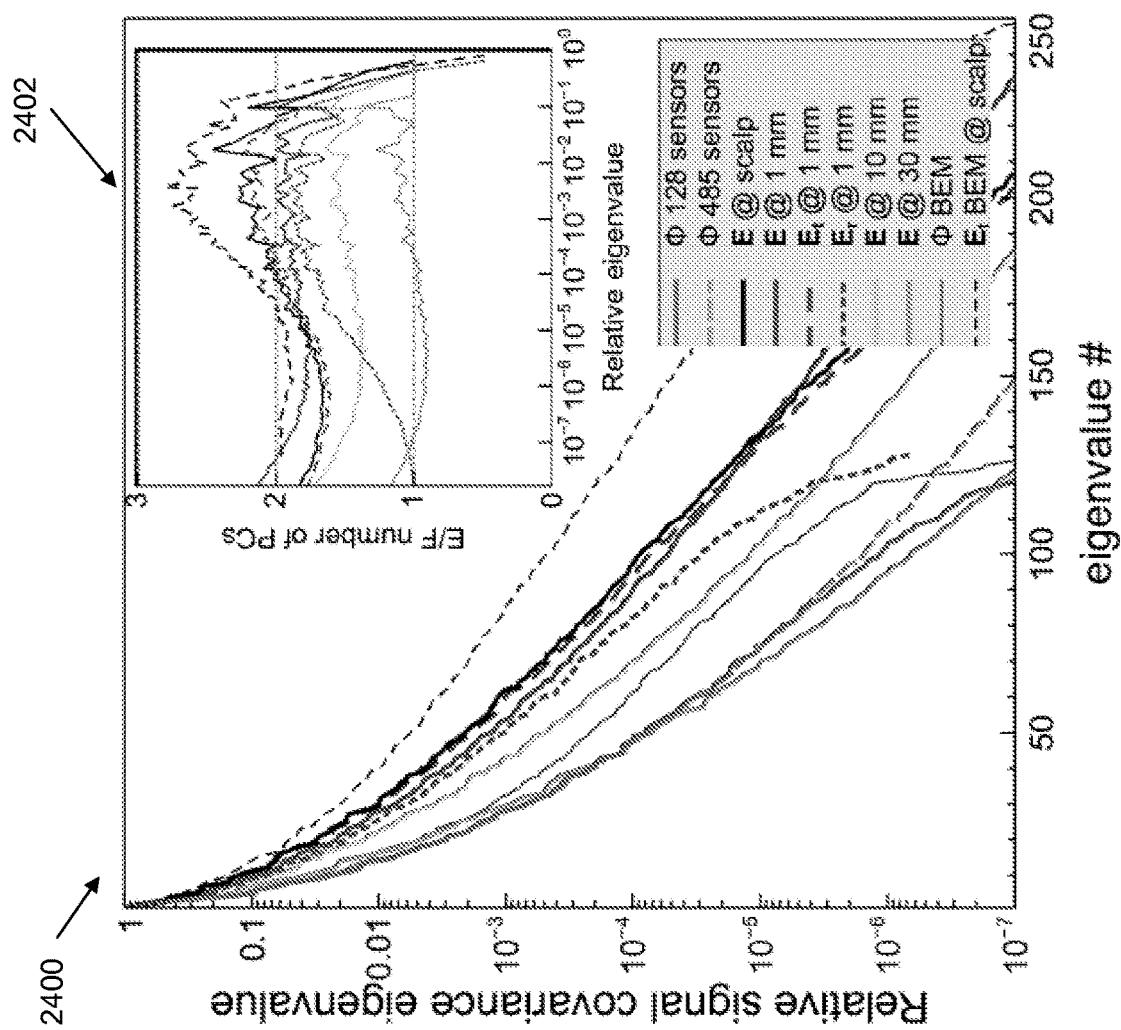
FIG. 24 illustrates normalized eigenvalues, in accordance with some embodiments.

FIG. 24 illustrates normalized eigenvalues of the data covariance matrix plotted in descending order 2400, in accordance with certain embodiments. One also wants to know how different components of electric field contribute to the number of usable signals. To this end, PCA analysis for EFEG sensors positioned 1 mm above the scalp surface may be repeated for radial ($E_r$) and tangential ($E\theta$ and $E\varphi$) components separately. EFEG sensors at different distances above the scalp surface (0 mm/scalp, 1 mm, 10 mm, 30 mm) were simulated. The inset 502 shows the ratio of the number of eigenvalues above a given value (plotted along the x-axis) between the electric field E and the potential $\Phi$ data. The number of sensors may be 128 and 256 for the two cases. The results are shown in FIG. 6 by the dotted and dashed blue curves respectively. Radial field alone offered almost two times more usable signals than the potential for the realistic noise-to-signal power range. This agrees with the radial field being more focused than potential (FIGS. 21 and 22).

Somewhat paradoxically, the tangential field provided more usable signals than the full field. This result is less surprising once sensor noise is considered. Apparently, the radial field which is more informative for radial sources (FIG. 21) contributed very little additional signal for tangential sources, and the amount of noise it may have added made its input somewhat disadvantageous. Note that most of the simulated brain sources were tangential. We consider a source dipole 'tangential' when its tangential component is larger than its radial component. Given that as a whole cortical normals are fairly randomly oriented, a simple calculation of solid angles shows that, proportionally, $1/\sqrt{2}$ or about 70% of cortical sources are tangential.

The largest increase in the number of signals between potential and field measurements was observed for the BEM head model. It fitted the brain closer and, therefore, it had smaller dipole—sensor distances compared to the spherical model. BEM head model produced less cortical current diffusion because it did not include the large gradient of conductance at the CSF—skull boundary. It also did not model the skull's anisotropy, which spreads the currents still further within the skull. One might also note that any deviation of the head model from spherical symmetry makes surface currents more characteristic of the underlying cortical sources. Altogether, these observations suggest that the more information is available the more advantage EFEG has over EEG.

3.3. Source Localization

Analysis presented in the previous section shows that high-density electric field measurements are more informative than potential measurements when done close to the head surface. Accordingly, a source localization algorithm may be able to reconstruct cortical sources more accurately when using electric field data. Localization errors of source reconstruction for the same 5,124 source patches as used in the previous section were calculated. Two source localization algorithms, MNE (Hämäläinen & Ilmoniemi, 1994) and Harmony (Petrov, 2012), were tested, the disclosures of these references are incorporated in this application in their entirety.

Both algorithms sought a 'distributed solution,' i.e., a pattern of activation distributed over thousands of cortical dipoles of fixed orientation and location (Section 2.8). Because for a 'distributed solution' the number of usable signals is much smaller than the number of cortical dipoles the inference problem is severely underdetermined, and some constraints may be used to make the solution unique. The two algorithms use different constraints: MNE chooses the solution with the least power (activation), while Harmony chooses the solution with the least high spatial frequency content. The rationale of the Harmony approach is that the high spatial frequency components of the solution cannot be reliably inferred from scalp data due to strong low-pass spatial filtering of the skull. A bonus is that the solution is smooth and coherent.

In order to account for sensor noise and correlations among sensors the source localization algorithms require an estimate of the noise-covariance matrix $\Sigma$. While such matrix can be estimated from experimental data for potential (EEG) sensors no such data may be available for electric field sensors. Instead, the simulated signal covariance matrix C given by (34) regularized by a small amount of uncorrelated internal sensor noise may be used:

$$\Sigma = \lambda(C + \epsilon I), \quad (35)$$

where I is the identity matrix, $\epsilon$ is the regularization constant defining the amount of internal sensor noise, and $\lambda$ is the overall noise scaling parameter defining the solution regularization. This choice of $\Sigma$ emulates noise from some (irrelevant) cortical activity plus the internal sensor noise. The c value used corresponded to 3% signal-to-noise ratio for the internal sensor noise, the particular choice may not be very important. The value of $\lambda$ may be more critical because this parameter determines how well the solution fits the data versus how well the solution fits the constraints of the localization algorithm. $\lambda$ may be chosen so as to minimize the mean localization error, separately for potential and field localizations, and for each algorithm.

The localization error may be calculated as follows. First, the location of the true source may be calculated by averaging the locations of its n=37 constituent dipoles. Then, n highest-amplitude dipoles were found in the solution for the same cortical hemisphere where the source is located. For each of the dipoles the distance $d_i$ between the dipole i and the source location may be calculated along the (pial) cortical surface. The raw localization error may then be taken as the weighted average of di:

$$e = \frac{\sum_{i=1}^{n} |x_i| \cdot d_i}{\sum_{i=1}^{n} |x_i|}, \qquad (36)$$

where xi stands for the solution magnitude for the i-th dipole. Finally, the raw localization error may be corrected for the extent of the true source e0, given by the above formula applied to the source patch itself:

$$LE = e - e_0. \qquad (37)$$

Figure 25:
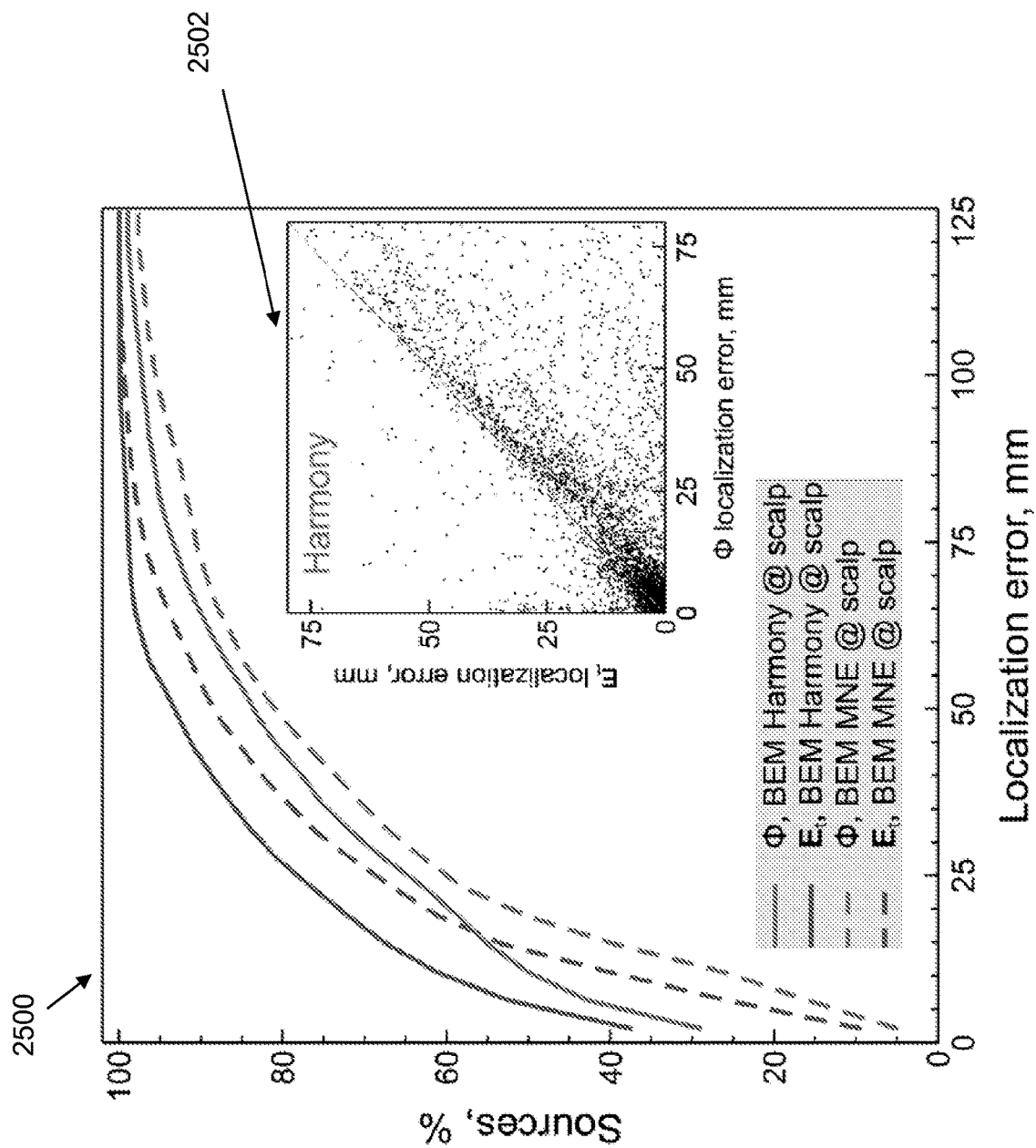
FIG. 25 illustrates source localization results, in accordance with some embodiments.

FIG. 25 illustrates source localization results for Harmony and MNE source localization algorithms, in accordance with certain embodiments. In chart 2502, the localization error, LE, is plotted along the x-axis. The percentage of sources reconstructed with localization error smaller than a given x-value is plotted along the y-axis. The inset 2504 shows Harmony localization error comparison between electric field and potential localizations. Each dot represents one of the 5124 simulated source patches. The LE value is plotted along the x-axis, and the percentage of sources localized with a smaller error than the given x-value is plotted along the y-axis. Only BEM head model results are shown, where Et calculated at the scalp surface may be used for electric field measurements. Spherical model results were similar and are not displayed. Harmony results are shown with solid lines, MNE results—with dashed lines. The inset shows a scatter plot of the Harmony localization errors for all simulated source patches comparing potential localization error (x-axis) and field localization error (y-axis).

The Harmony localization error decreased approximately two-fold between potential and field measurements for sources localized with less than 3 cm error. This included about ⅔ of all sources and can be seen as the shift of the blue curve upwards with respect to the red curve, and also as the tendency for most of the dots in the inset to fall well below the diagonal line near the plot's origin. For the remaining sources the improvement is less dramatic but still very significant. The MNE algorithm showed qualitatively similar results, but it performed poorer than Harmony and its localization may be less improved between potential and field measurements.

The foregoing has outlined some of the more pertinent features of the subject matter. These features should be construed to be merely illustrative. Many other beneficial results can be attained by applying the disclosed subject matter in a different manner or by modifying the subject matter as will be described. For example, the amplifier circuit may be miniaturized to reduce cost and space requirements.

The invention claimed is:

1. A method for measuring brain activity of a subject, comprising:
    positioning a plurality of electric field sensors at multiple positions exterior to a skull of the subject, each sensor comprising two or more pin electrodes in electrical contact with a scalp of the subject and positioned to measure tangential and radial components of electric field vectors generated by the brain activity of the subject;
    measuring tangential and radial components of a plurality of instantaneous electric field vectors generated by a plurality of electric field sources, the instantaneous electric field vectors being measured by the plurality of electric field sensors;
    determining, by a computer comprising at least one processor and a memory providing code, the computer in communication with the plurality of electric field sensors, electric field brain activity, the determining comprising;
    identifying sources of electric fields within the brain of the subject based on the measurement of the tangential and radial components of the plurality of instantaneous electric field vectors, and
    estimating a location of each electric field source within the brain from the tangential and radial electric field components generated from the plurality of electric field sources using a mathematical model of head electrical characteristics for estimating three-dimensional location data, each electric field source corresponding to a distinguishable data channel, and
    generating a real-time multi-channel image of the electric field brain activity.

2. The method of claim 1, wherein the subject suffers from a neurological condition.

3. The method of claim 1, wherein the subject suffers from Alzheimer's disease, traumatic brain injury, autism, or epilepsy.

4. The method of claim 1 further comprising comparing the electric field brain activity of the subject to the electric field brain activity of a normal subject.

5. The method of claim 4 further comprising detecting a neurological condition based on the comparison of the electric field brain activity of the subject to the electric field brain activity of the normal subject.

6. The method of claim 1, wherein the image is a three-dimensional image of the electric field sources in the brain of the subject.

7. The method of claim 1, further comprising performing noisiness estimation for each electric field sensor by cross-correlating information from each of the plurality of electric field sensors.

8. The method of claim 1, wherein the plurality of electric field sensors include tri-polar or multi-polar electrode sensors for measuring the tangential and radial components of the electric field vectors at each sensor.

9. The method of claim 8, wherein the tri-polar electrode sensors are made of silver chloride (AgCl).

10. The method of claim 1 further comprising repeating measuring the components of an electric field vector to monitor brain activity over time.

11. The method of claim 1, wherein estimating a location of each electric field source provides a time resolution of 1 millisecond.

12. The method of claim 1 further comprising measuring a signal from the plurality of electric field sensors in real-time to determine noise levels.

13. The method of claim 1 further comprising displaying a pattern that is viewed by the subject while simultaneously measuring a plurality of instantaneous electric field vectors.

14. The method of claim 1, wherein the mathematical model of head electrical characteristics comprises a model of dipole current sources described by electric field components, and the tangential and radial electric field components generated from the plurality of electric field sources are applied to the model to reconstruct the electric field sources of the brain of the subject.

15. The method of claim 1, wherein the instantaneous electric field vectors measured by each sensor are given by negative gradients of electric potential between the two or more pin electrodes of each sensor.

16. The method of claim 1, wherein each sensor includes at least three electrodes, and one of the three electrodes is a reference electrode.

17. A sensor apparatus for monitoring brain activity of a subject, comprising:
- a plurality of electric field sensors configured to measure a plurality of instantaneous electric field vectors generated by electric field brain activity of the subject, each sensor comprising two or more pin electrodes configured to be disposed for electrical contact with a scalp of the subject and positioned to measure tangential and radial components of the instantaneous electric field vectors, the plurality of electric field sensors configured to be distributed evenly at a plurality of locations exterior to a skull of the subject;
- a computer for processing the measured electric field vectors, the computer comprising at least one processor and a memory providing code to the at least one processor configured to:
  (i) estimate the noisiness of each electric field sensor using data from at least one of the plurality of electric field sensors,
  (ii) identify sources of electric fields within the brain of the subject based on the measurement of the tangential and radial components of the measured electric field vectors,
  (iii) estimate a three-dimensional location for each electric field source within the brain from the tangential and radial electric field components generated from the plurality of electric field sources using a mathematical model of head electrical characteristics for estimating three-dimensional location data, each electric field source corresponding to a distinguishable data channel, and
  (iv) generate a real-time, multi-channel image of brain activity.

18. The sensor apparatus of claim 17, the plurality of electric field sensors further comprising at least 128 sensors.

19. The sensor apparatus of claim 18, further comprising a cap for conforming to the shape of the skull in which the plurality of sensors are embedded.

20. The sensor apparatus of claim 17, wherein the apparatus comprises at least one conduit for transmitting the measured electric field vectors measured by the electric field sensors to the computer.

21. The sensor apparatus of claim 17 further comprising a display for the subject to visualize a pattern.

22. The sensor apparatus of claim 17, wherein the plurality of electric field sensors include tri-polar electrode sensors.

23. The sensor apparatus of claim 22, wherein the tri-polar electrode sensors are made of silver chloride (AgCl).

24. The sensor apparatus of claim 22, wherein the tri-polar electrode sensors are 1-15 mm long and separated by 1-15 mm distances.

25. The sensor apparatuses of claim 22, wherein the tri-polar electrode sensors are attached to a plastic disk.

26. The sensor apparatus of claim 17, wherein the mathematical model of head electrical characteristics comprises a model of dipole current sources described by electric field components, and the tangential and radial electric field components generated from the plurality of electric field sources are applied to the model to reconstruct the electric field sources of the brain of the subject.

27. The sensor apparatus of claim 17, wherein the instantaneous electric field vectors measured by each sensor are given by negative gradients of electric potential between the two or more pin electrodes of each sensor.

28. The sensor apparatus of claim 17, wherein each sensor includes at least three electrodes, and one of the three electrodes is a reference electrode.

* * * * *